(12) United States Patent
Lee et al.

(10) Patent No.: US 9,524,703 B2
(45) Date of Patent: *Dec. 20, 2016

(54) METHOD OF OPERATING AN ELECTRONIC DEVICE PROVIDING A BIOEFFECT IMAGE

(71) Applicant: SAMSUNG DISPLAY CO., LTD., Yongin, Gyeonggi-Do (KR)

(72) Inventors: Chang-Hoon Lee, Seoul (KR); IL-Nam Kim, Hwaseong-si (KR); Jong-In Baek, Suwon-si (KR); Yi-Joon Ahn, Seoul (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 35 days.

This patent is subject to a terminal disclaimer.

(21) Appl. No.: 14/589,035

(22) Filed: Jan. 5, 2015

(65) Prior Publication Data

US 2015/0356954 A1    Dec. 10, 2015

(30) Foreign Application Priority Data

Jun. 10, 2014 (KR) ........................ 10-2014-0070024

(51) Int. Cl.
| | |
|---|---|
| G09G 5/377 | (2006.01) |
| G06K 9/20 | (2006.01) |
| G06T 13/80 | (2011.01) |
| G06F 3/041 | (2006.01) |
| G06F 3/0354 | (2013.01) |
| G06F 3/02 | (2006.01) |

(Continued)

(52) U.S. Cl.
CPC ................ *G09G 5/377* (2013.01); *A61N 5/06* (2013.01); *G06F 3/013* (2013.01); *G06F 3/0227* (2013.01); *G06F 3/03543* (2013.01); *G06F 3/041* (2013.01); *G06F 19/34* (2013.01); *G06F 19/3406* (2013.01); *G06K 9/2081* (2013.01); *G06T 13/80* (2013.01); *A61N 2005/0626* (2013.01); *G09G 2354/00* (2013.01); *G09G 2380/08* (2013.01)

(58) Field of Classification Search
None
See application file for complete search history.

(56) References Cited

U.S. PATENT DOCUMENTS 6,873,327 B1 * 3/2005 Edwards ................. G06T 11/60
345/473
7,446,762 B2   11/2008 Hsieh et al.
(Continued)

FOREIGN PATENT DOCUMENTS

| JP | 08-242411 | 9/1996 |
|---|---|---|
| JP | 2000-339438 | 12/2000 |

(Continued)

OTHER PUBLICATIONS

Patrick Polatsek, Blink Rate Tracking of Computer User, May 31, 2013, pp. 1-76.

(Continued)

*Primary Examiner* — Kimberly A Williams
(74) *Attorney, Agent, or Firm* — Lee & Morse, P.C.

(57) ABSTRACT

A method of operating an electronic device includes displaying a first image, extracting a user-interested region from a region including the first image, and displaying a bioeffect image at the user-interested region. The first image and bioeffect image are different images.

17 Claims, 25 Drawing Sheets

(51) Int. Cl.
*G06F 3/01* (2006.01)
*A61N 5/06* (2006.01)
*G06F 19/00* (2011.01)

(56) References Cited

U.S. PATENT DOCUMENTS

| | | | |
|---|---|---|---|
| 7,487,529 | B1 | 2/2009 | Orlick et al. |
| 8,634,673 | B1 | 1/2014 | McDougal et al. |
| 2005/0220321 | A1 | 10/2005 | Langelaar |
| 2006/0189879 | A1* | 8/2006 | Miyajima ............ A61B 5/1135 600/534 |
| 2007/0268234 | A1 | 11/2007 | Wakabayashi et al. |
| 2008/0143739 | A1 | 6/2008 | Harris et al. |
| 2008/0259098 | A1* | 10/2008 | Zamorsky ................ A61H 5/00 345/690 |
| 2010/0058229 | A1 | 3/2010 | Mercer |
| 2011/0298702 | A1 | 12/2011 | Sakata et al. |
| 2013/0083215 | A1* | 4/2013 | Wisniewski ....... H04N 5/23222 348/222.1 |
| 2013/0141439 | A1* | 6/2013 | Kryzhanovsky ........ G06T 13/80 345/473 |
| 2013/0216204 | A1 | 8/2013 | Kulakov |
| 2015/0220157 | A1* | 8/2015 | Marggraff ............... G06F 3/017 345/156 |
| 2016/0012622 | A1* | 1/2016 | Lee ......................... G06T 11/60 345/629 |

FOREIGN PATENT DOCUMENTS

| | | |
|---|---|---|
| KR | 10-1999-0048705 A | 7/1999 |
| KR | 10-20000049412 A | 8/2000 |
| KR | 10-2001-0091322 A | 10/2001 |
| KR | 10-0434894 | 5/2004 |
| KR | 10-2005-0089649 A | 9/2005 |
| KR | 10-2009-0002306 A | 1/2009 |
| KR | 10-2012-0124256 A | 11/2012 |
| KR | 10-2015-0135660 A | 12/2015 |
| WO | WO 2013/065900 A1 | 5/2013 |
| WO | WO 2013062180 A | 5/2013 |

OTHER PUBLICATIONS

EyeLeo Prevents eye strain, Sep. 7, 2013.
European Office Action dated Oct. 30, 2015.
Fawad Mir, "Fotowall is Easy-To-Use Application for Creating Photo Collages "http://www.addictivetips.com/windows-tips/fotowall-is-easy-to-use-application-for-creating-photo-collages/, Dec. 28, 2011.
Duff et al. "Compositing Digital Images," Computer Graphics Project, Lucasfilm Ltd., ACM, 1984.
"Visolve for Windows" http://www.ryobi-sol.co.jp/visolve/windows/en/.
European Office Action dated Sep. 8, 2016 in Corresponding European Patent Application No. 15156262.6.

* cited by examiner

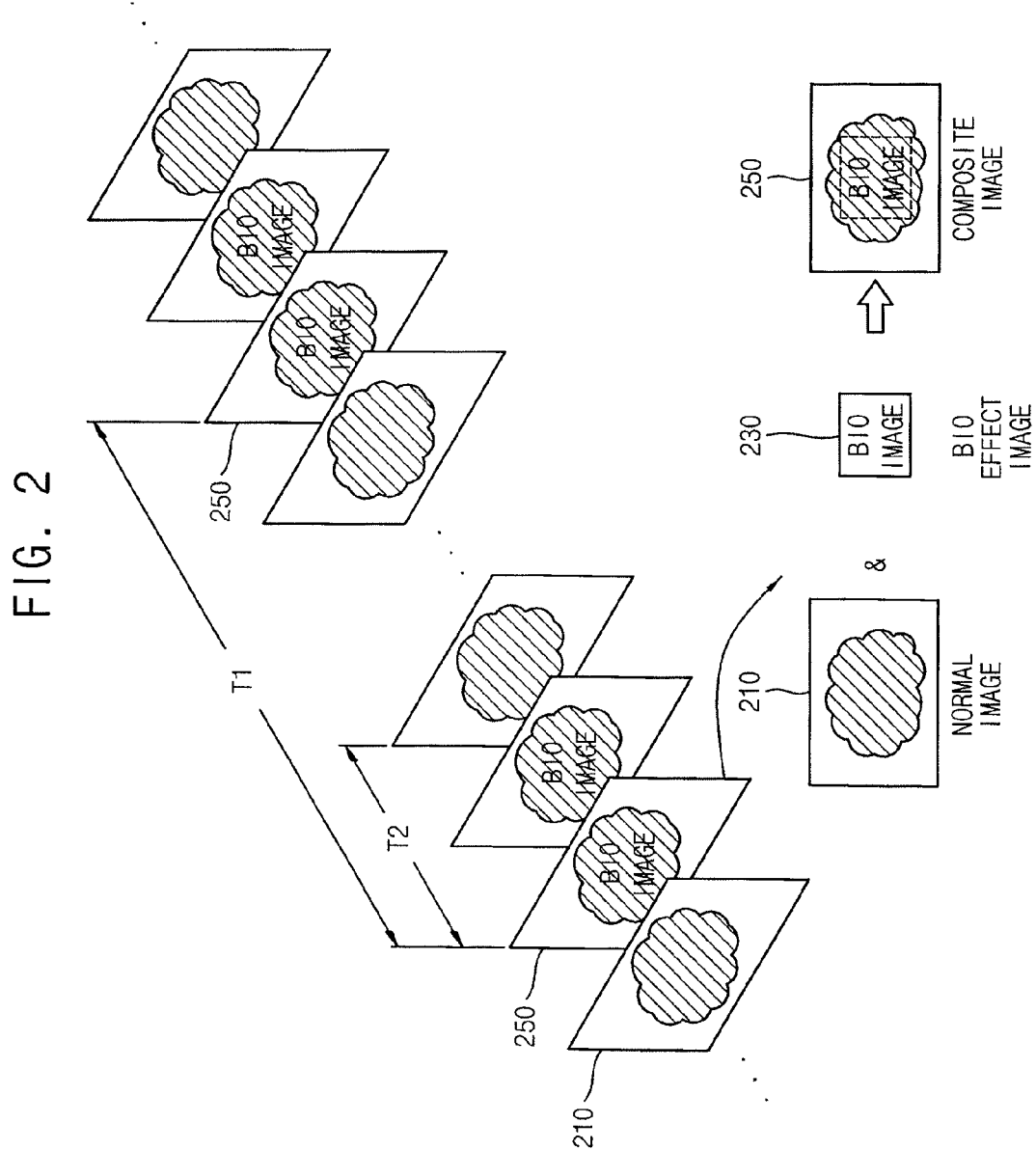

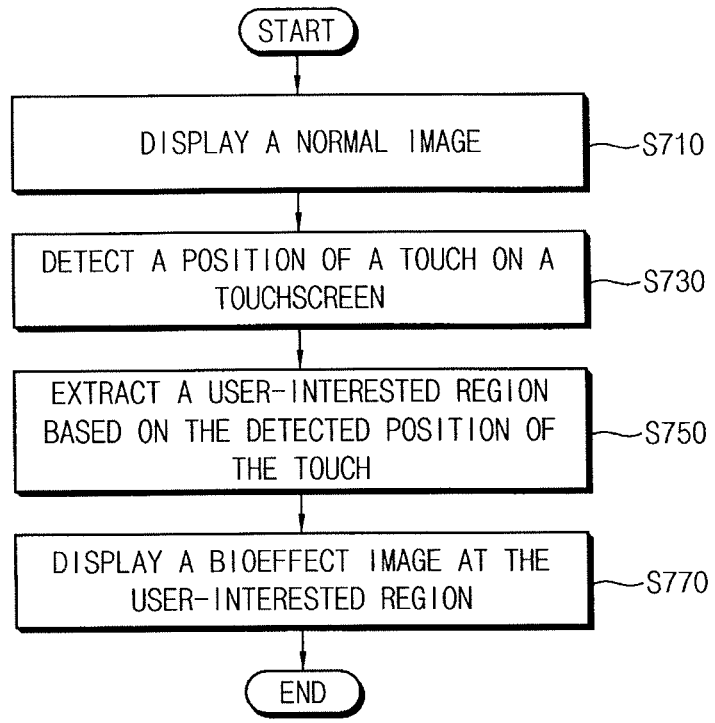
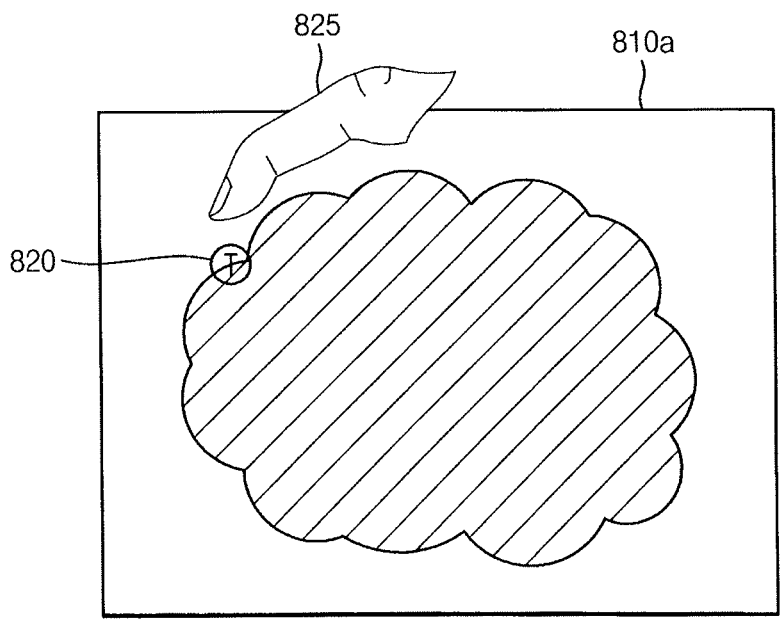

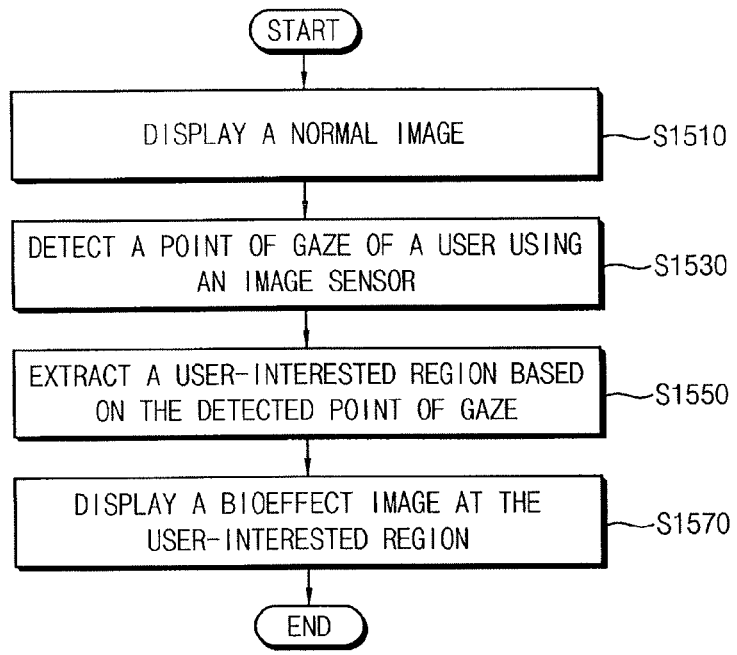
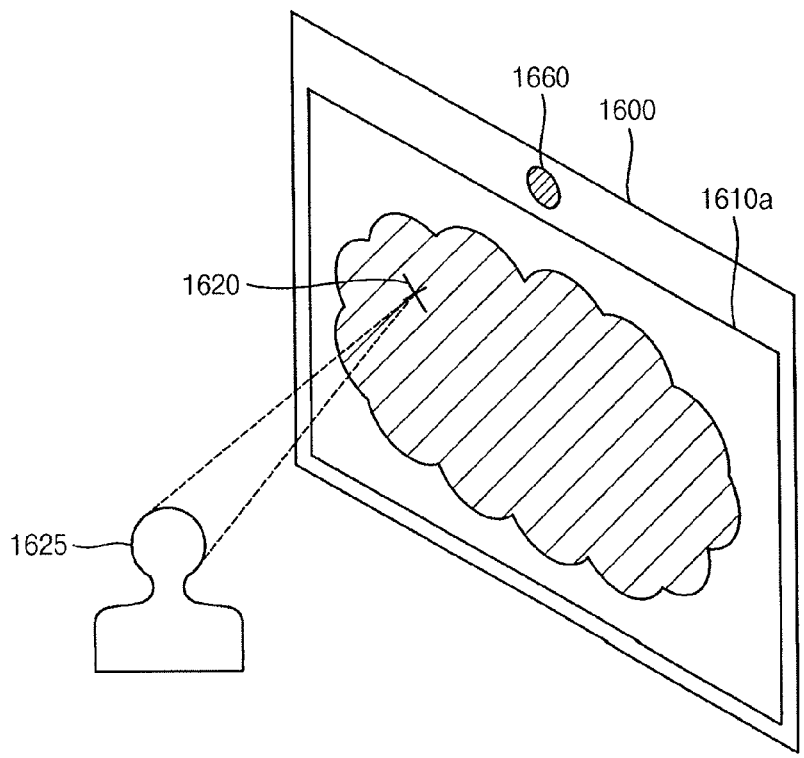

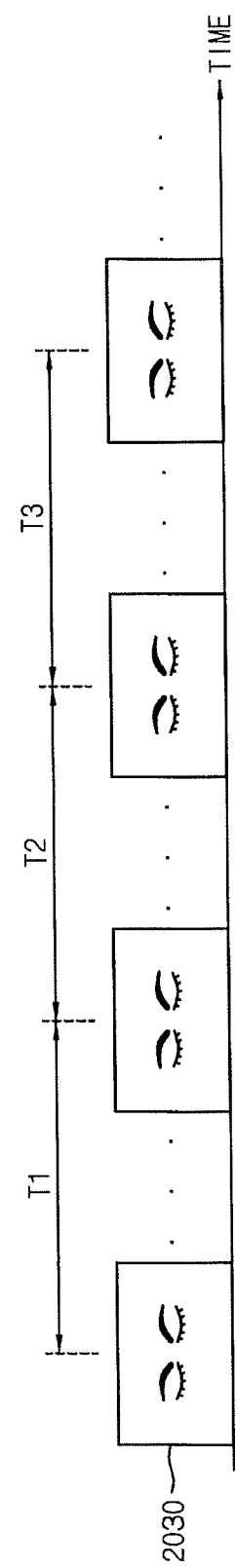

METHOD OF OPERATING AN ELECTRONIC DEVICE PROVIDING A BIOEFFECT IMAGE

CROSS REFERENCE TO RELATED APPLICATION

Korean Patent Application No. 10-2014-0070024, filed on Jun. 10, 2014, and entitled, "Method of Operating an Electronic Device Providing a Bioeffect Image," is incorporated by reference herein in its entirety.

BACKGROUND

1. Field

One or more embodiments described herein relate to a method of operating an electronic device providing a bioeffect image.

2. Description of the Related Art

Photo-therapy and other bioeffect devices that radiate light on a human body have been developed. These devices may be used, for example, to provide anti-inflammatory therapy, pimple therapy, wrinkle therapy, skin lightening therapy, biorhythm control, or depression therapy. However, each bioeffect device provides only one particular type of treatment. As a result, a user must purchase different bioeffect devices for different treatments. Furthermore, bioeffect devices are not able to display other images (such as visual images) while a user is undergoing treatment.

SUMMARY

In accordance with one embodiment, a method of operating an electronic device includes displaying a first image; extracting a user-interested region from a region including the first image; and displaying a bioeffect image at the user-interested region, wherein the first image and the bioeffect image are different images.

Extracting the user-interested region may include detecting a position designed by an input device and extracting the user-interested region based on the detected position. The input device may be a computer mouse, and the detected position may be a pointer position of the computer mouse. The input device may be a keyboard, and the detected position may be a cursor position of the keyboard. The input device may be a touchscreen, and the detected position may be a position of a touch on the touchscreen. The input device may be a pointing device, and the detected position may be a position pointed by the pointing device.

Extracting the user-interested region may include detecting a plurality of positions designated by an input device during a plurality of frames; calculating an average position by averaging the positions; and extracting the user-interested region based on the average pointed position.

Extracting the user-interested region may include dividing the region where the normal image is displayed into a plurality of regions; detecting a position designated by an input device; and extracting one of the regions corresponding to the detected position as the user-interested region.

Extracting the user-interested region may include detecting a point of gaze of a user; and extracting the user-interested region based on the point of gaze.

The method may include applying an animation effect to the bioeffect image. The animation effect may include at least one of an appear effect, a fly-in effect, a float-in effect, a grow effect a shrink effect, a brightness change effect, or a rotation effect. The bioeffect image may be displayed for a duration shorter than a duration perceptible by a user. The bioeffect image may be periodically displayed. At least one of a period of the bioeffect image or a duration of the bioeffect image may vary. The bioeffect image may include at least one of a behavior inducing image, a photo-therapy image, a biorhythm control image, or a color weakness compensation image.

The bioeffect image may include an eye-blink inducing image to induce eye blinking of a user. The method may include detecting an eye-blink pattern and displaying the eye-blink inducing image based on the eye-blink pattern. The method may include calculating an average eye-blink period based on a detected eye-blink pattern, and displaying the eye-blink inducing image if the average eye-blink period is longer than a predetermined time.

The method may include calculating an average eye-blink period based on a detected eye-blink pattern, and displaying the eye-blink inducing image if the average eye-blink period is longer than a first time, the eye-blink inducing image displayed based on a pattern having an average period that decreases at a predetermined rate from the first time to a second time shorter than the first time.

In accordance with another embodiment, a method of operating an electronic device includes displaying a first image, extracting a user-interested region from a region including the first image, and displaying an eye-blink inducing image at the user-interested region, wherein the first image and eye-blink inducing image are different images.

In accordance with another embodiment, an apparatus includes an output and a processor coupled to the output to control display of information, wherein the processor is to control operations which include displaying a first image, extracting a user-interested region from a region including the first image, and displaying a bioeffect image at the user-interested region, wherein the first image and the bioeffect image are different images.

In accordance with another embodiment, a computer-readable medium storing code for controlling display of information, the code including: first code to display a first image; second code to extract a user-interested region from a region including the first image, and third code to display a bioeffect image at the user-interested region, wherein the first image and the bioeffect image are different images.

BRIEF DESCRIPTION OF THE DRAWINGS

Features will become apparent to those of skill in the art by describing in detail exemplary embodiments with reference to the attached drawings in which:

FIG. 2 illustrates an example of image frames produced by the method;

FIG. 9 illustrates another embodiment of a method of providing a bioeffect image;

FIG. 10A illustrates another example of extracting a user-interested region.

FIG. 17 illustrates another method for providing a bioeffect image;

FIG. 18A illustrates another example of extracting a user-interested region.

FIG. 22B illustrates an example of an eye-blink inducing image displayed based on the detected eye-blink pattern;

DETAILED DESCRIPTION

Figure 1:
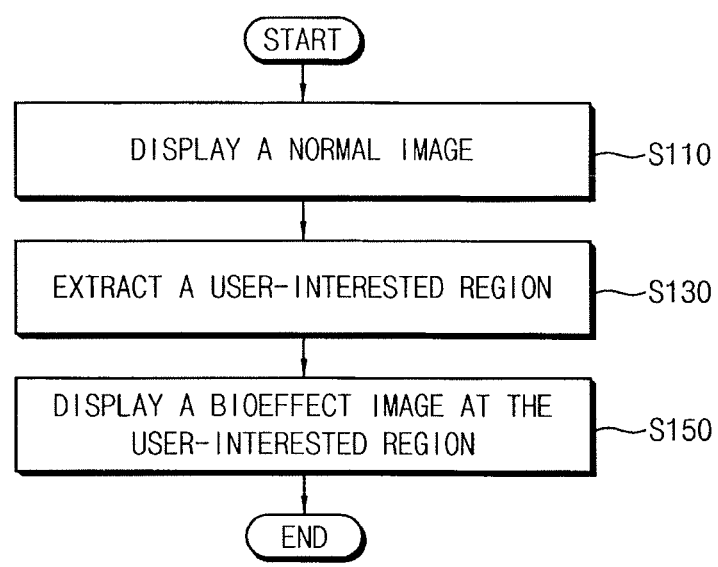
FIG. 1 illustrates an embodiment of a method for providing a bioeffect image.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawings, the dimensions of layers and regions may be exaggerated for clarity of illustration. Like reference numerals refer to like elements throughout.

Figure 3A:
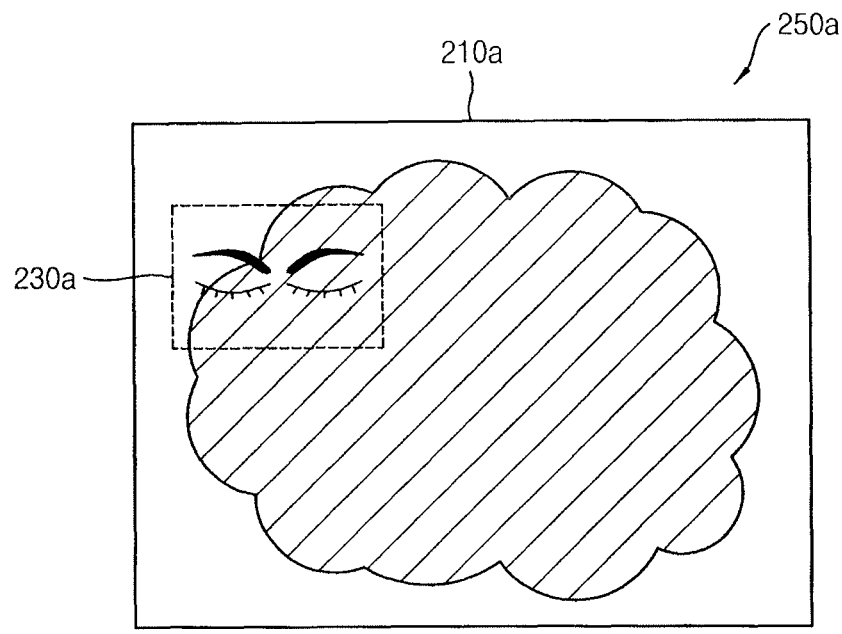
FIG. 3A-3C illustrate examples of bioeffect images.
Figure 3B:
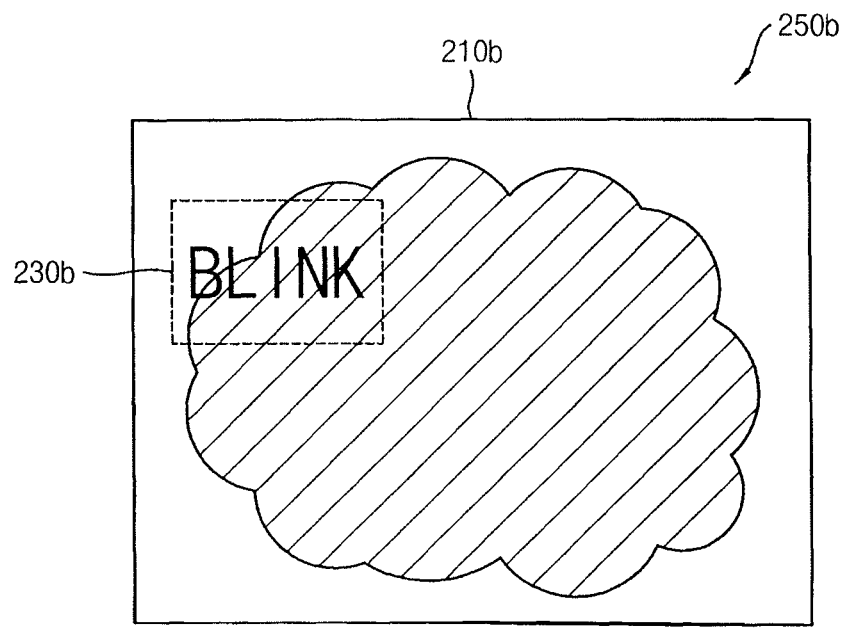
Figure 3C:
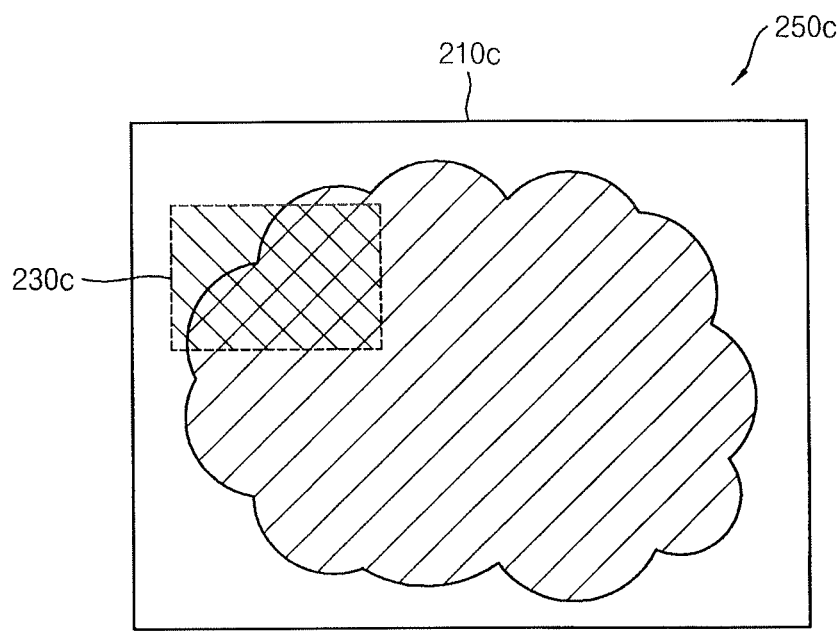
Figure 4A:
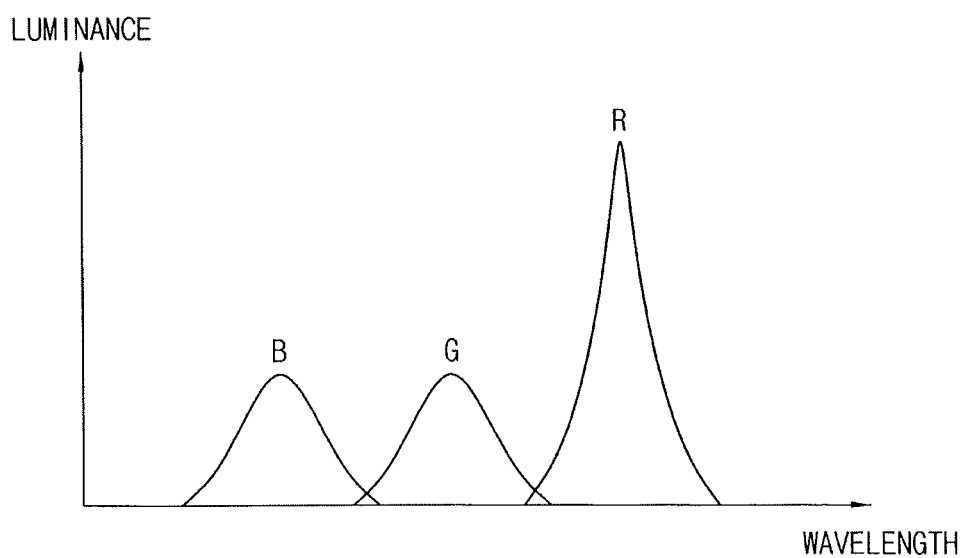
FIG. 4A-4C illustrate additional examples of bioeffect images.
Figure 4B:
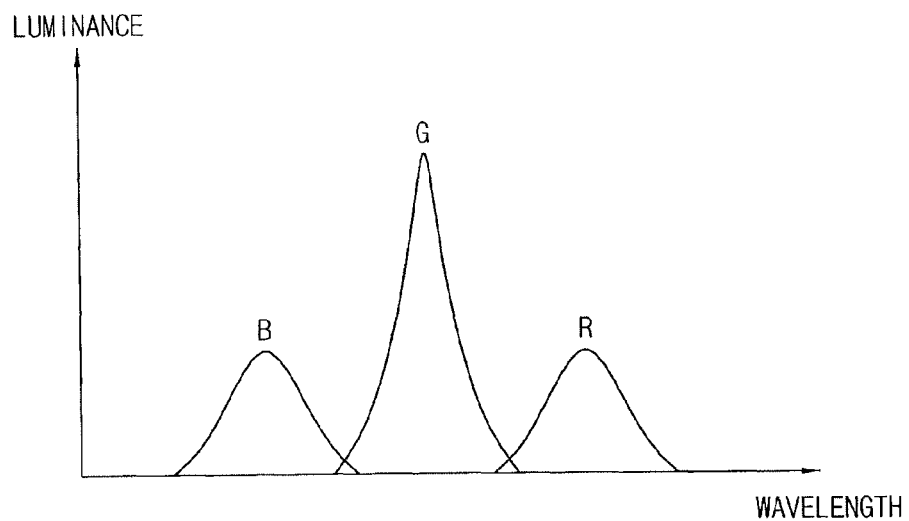
Figure 4C:
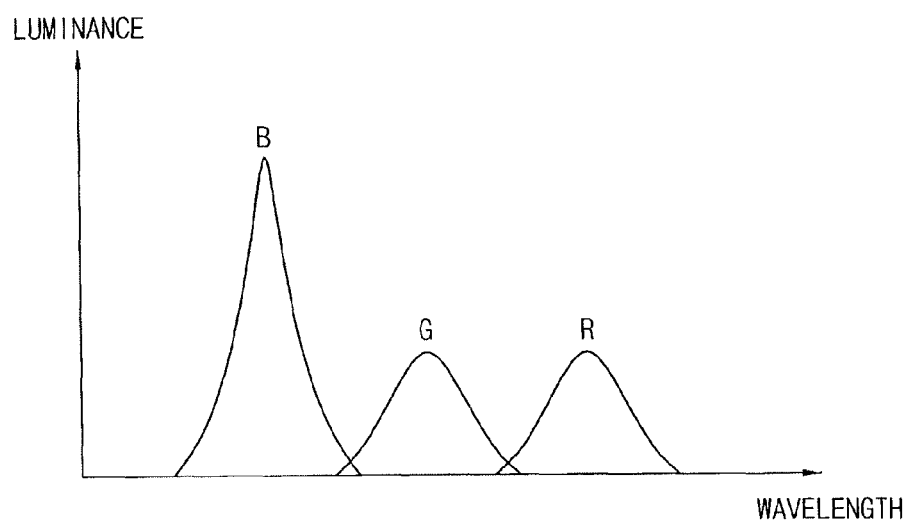

FIG. 1 illustrates an embodiment of a method for operating an electronic device to provide a bioeffect image using a display device. FIG. 2 illustrates an example of image frames displayed by this method. FIG. 3A to 3C illustrate examples of bioeffect images displayed by the method. FIG. 4A to 4C are graphs describing examples of bioeffect images displayed by the method.

Referring to FIG. 1, an electronic device displays a normal image using a display device (S110). The normal image may be an image that the electronic device displays for an original purpose of the electronic device. For example, when the electronic device is a digital television (TV) or a smart TV, the normal image may be a TV program image broadcasted by a TV station. When the electronic device is a smart phone, the normal image may be an image of an application executed at the smart phone.

In other embodiments, the electronic device may be any electronic device including a display device. Examples include but are not limited to a cellular phone, a smart phone, a tablet computer, a personal digital assistant, a portable multimedia player, a digital camera, a music player, a portable game console, a navigation system, a personal computer, a laptop computer, a server computer, a workstation, a digital television, and a set-top box.

The electronic device may extract a user-interested region from a display region of the display device, e.g., a region where the normal image is displayed (S130). In one embodiment, the electronic device may detect a position designated by an input device of the electronic device, and may extract the user-interested region based on this position. For example, the electronic device may extract the user-interested region based on the pointer position of a computer mouse, the cursor position of a computer keyboard, the position of a touch on a touchscreen, and/or the position pointed by a pointing device. Also, the electronic device may detect the point of gaze of a user using an image sensor, and may extract the user-interested region based on the detected point of gaze.

The electronic device displays a bioeffect image at the user-interested region using the display device (S150). For example, the electronic device may display the bioeffect image instead of the normal image at the user-interested region, and may display the normal image at a remaining or another region. In another embodiment, the electronic device may synthesize or overlay the bioeffect image and the normal image at the user-interested region, and may display the normal image at a remaining or another region.

For example, as illustrated in FIG. 2, while displaying the normal image 210 by using the display device, the electronic device may display, with a predetermined period T1, the bioeffect image 230 or a synthesized image 250 where the normal image 210 and the bioeffect image 230 are synthesized. In one embodiment, the bioeffect image 230 or the synthesized image 250 may be periodically displayed for a predetermined duration T2 each time. In another embodiment, at least one of the period T1 (or a time interval between two bioeffect images 230) or the duration T2 (or a time during which each bioeffect image is displayed) of the bioeffect image 230 or the synthesized image 250 may vary.

In one embodiment, the bioeffect image 230 may be a behavior inducing image for inducing a predetermined behavior of a user. For example, the bioeffect image 230 may be an image that induces a user to blink his eyes. In another example, as illustrated in FIG. 3A, the electronic device may display a synthesized image 250a where a normal image 210a and an image 230a of closed eyes are synthesized at the user-interested region. In another example, as illustrated in FIG. 3B, the electronic device may display a synthesized image 250b where a normal image 210*b* and a text image 230*b* that instructs eye-blinking are synthesized at the user-interested region.

These eye-blink inducing images 230*a* and 230*b* may induce the user to blink his eyes, for example, by a conformity effect or subliminal learning. In one embodiment, the bioeffect image 230 may be displayed for a duration shorter than a duration that is consciously perceptible by a user. For example, the eye-blink inducing images 230*a* and 230*b* may be displayed during one frame per the predetermined period T1. In this case, the eye-blink inducing images 230*a* and 230*b* may not be consciously perceived by the user, and thus the user will not be inconvenienced. However, because the eye-blink inducing images 230*a* and 230*b* are provided as a subliminal stimulus to the user, the eye-blink inducing images 230*a* and 230*b* may induce eye-blinking of the user by the conformity effect or the subliminal learning.

In another embodiment, the bioeffect image 230 may be a photo-therapy image, a biorhythm control image, or a color weakness compensation image. For example, as illustrated in FIG. 3C, the electronic device may display a synthesized image 250*c* where a bioeffect image 230*c* (e.g., a photo-therapy image, a biorhythm control image, a color weakness compensation image, etc.) is synthesized with a normal image 230*c* at a user-interested region.

In one embodiment, at least one of red luminance R, green luminance G, or blue luminance B of the bioeffect image 230*c* may be higher than the others. For example, as illustrated in FIG. 4A, the bioeffect image 230*c* may have relatively high red luminance R. In this case, the bioeffect image 230*c* may be the photo-therapy image (e.g., a pimple therapy image, a wrinkle therapy image, a skin lightening therapy image, etc.), or may be a color weakness compensation image that enhances visibility of a user having red color weakness.

In another example, as illustrated in FIG. 4B, the bioeffect image 230*c* may have relatively high green luminance G. In this case, the bioeffect image 230*c* may be a photo-therapy image such as a skin lightening therapy image, or may be a color weakness compensation image that enhances visibility of a user having green color weakness.

In another example, as illustrated in FIG. 4C, the bioeffect image 230*c* may have relatively high blue luminance B. In this case, the bioeffect image 230*c* may be a photo-therapy image such as a depression therapy image, a sterilization therapy image, etc., or may be a biorhythm control image that suppresses melatonin secretion of a user.

In another example, the bioeffect image 230*c* may be generated by decreasing at least one of red luminance R, green luminance G, or blue luminance B of the normal image 210*c*. For example, the bioeffect image 230*c* may be generated by decreasing the blue luminance B of the normal image 210*c*. In this case, the bioeffect image 230*c* having the decreased blue luminance B may be a biorhythm control image that prevents suppression of melatonin secretion of a user.

As described above, one or more of the aforementioned method embodiments provide a bioeffect image to the user while displaying a normal image. Further, one or more of the aforementioned method embodiments may display a bioeffect image at a user-interested region (e.g., corresponding to a position designated by an input device or corresponding to where a user is looking), thereby enhancing the effect by the bioeffect image.

Figure 5:
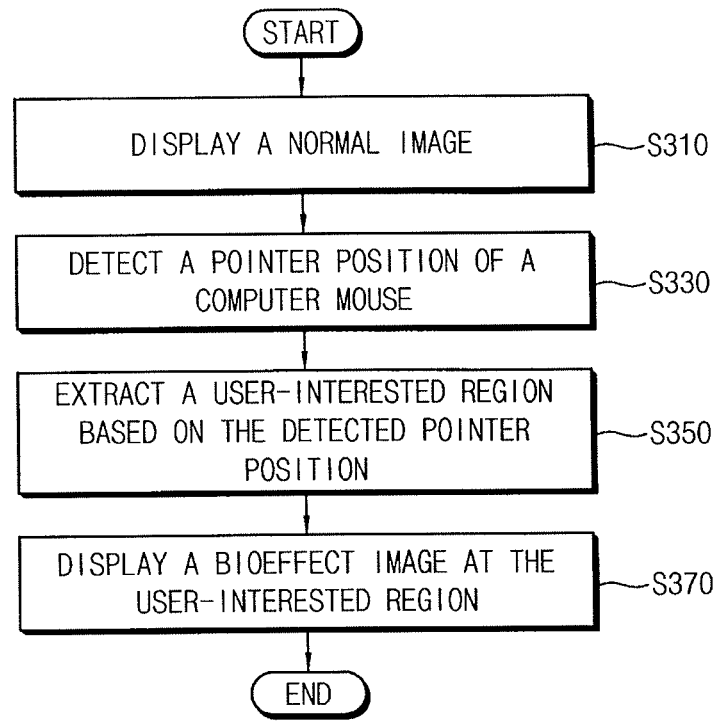
FIG. 5 illustrates another method for providing a bioeffect image.
Figure 6A:
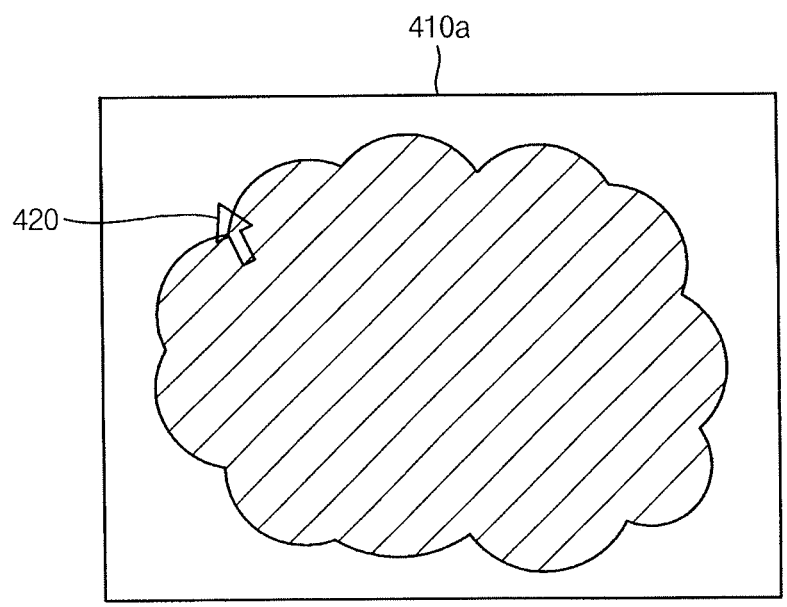
FIG. 6A illustrates an example of extracting a user-interested region.
Figure 6B:
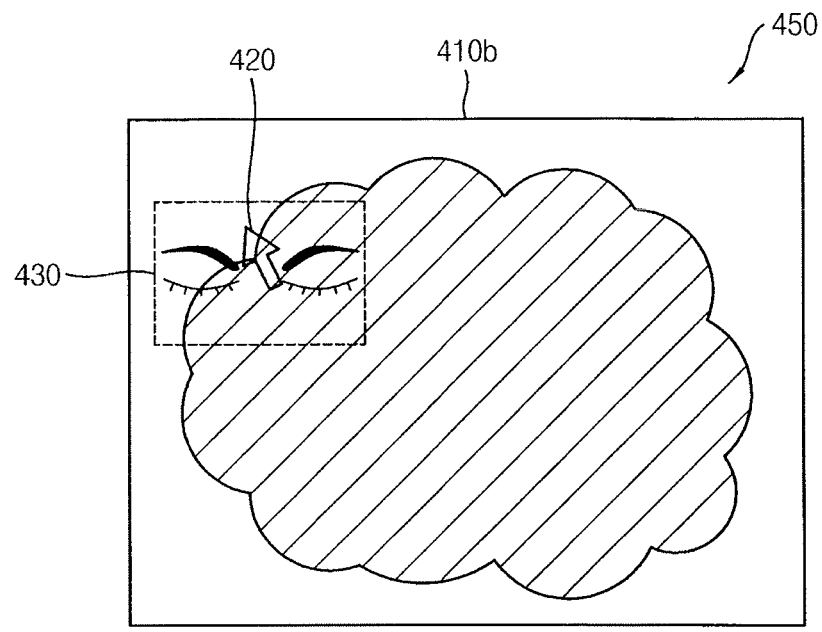
FIG. 6B illustrates an example of a bioeffect image at a user-interested region in FIG. 6A.

FIG. 5 illustrates another embodiment of a method for operating an electronic device to provide a bioeffect image using a display device. FIG. 6A illustrates an example of extracting a user-interested region, and FIG. 6B illustrates an example of a bioeffect image displayed at a user-interested region in FIG. 6A.

Referring to FIG. 5, an electronic device displays a normal image of the original purpose of the electronic device using a display device (S310). The electronic device may detect the position or coordinates of a pointer of a computer mouse of the electronic device (S330), and may extract a user-interested region from a region where the normal image is displayed based on the detected pointer position (S350). For example, as illustrated in FIG. 6A, the electronic device may detect the position of the pointer 420 of the computer mouse at the normal image 410*a*, and may determine, as the user-interested region, a region having the detected position as a center point, a vertex, or the like.

The electronic device may display a bioeffect image at the user-interested region on the display device (S370). In one embodiment, the electronic device may display the bioeffect image instead of the normal image at the user-interested region. In another embodiment, the electronic device may synthesize or overlay the bioeffect image and the normal image at the user-interested region. For example, as illustrated in FIG. 6B, the electronic device may display a synthesized image 450 where a bioeffect image 430 (e.g., an eye-blink inducing image) is synthesized to a normal image 410*b* at the user-interested region determined based on the detected position of the pointer 420.

The aforementioned embodiment may therefore extract a user-interested region based on the pointer position of the computer mouse, and may display the bioeffect image at the user-interested region, to thereby enhance the effect by the bioeffect image.

Figure 7:
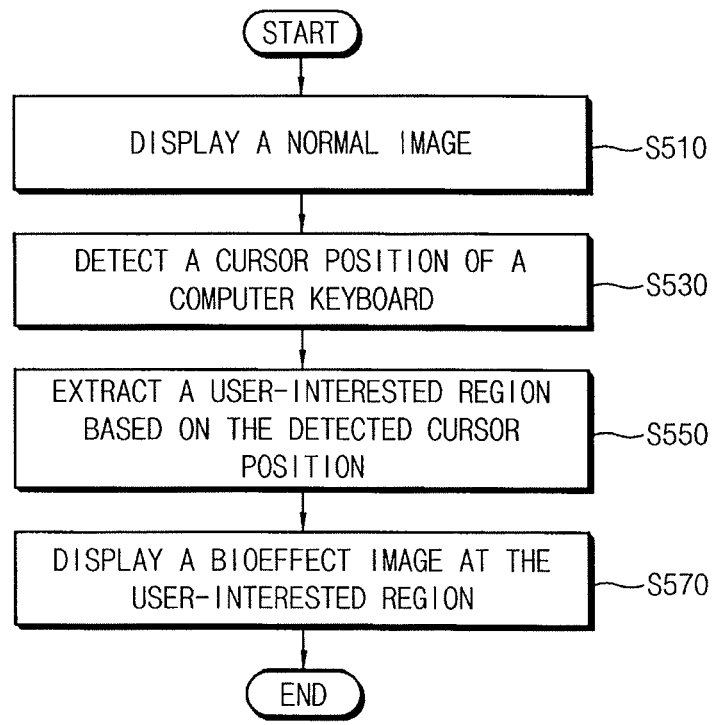
FIG. 7 illustrates another embodiment of a method for providing a bioeffect image.
Figure 8A:
FIG. 8A illustrates another example of extracting a user-interested region.
Figure 8B:
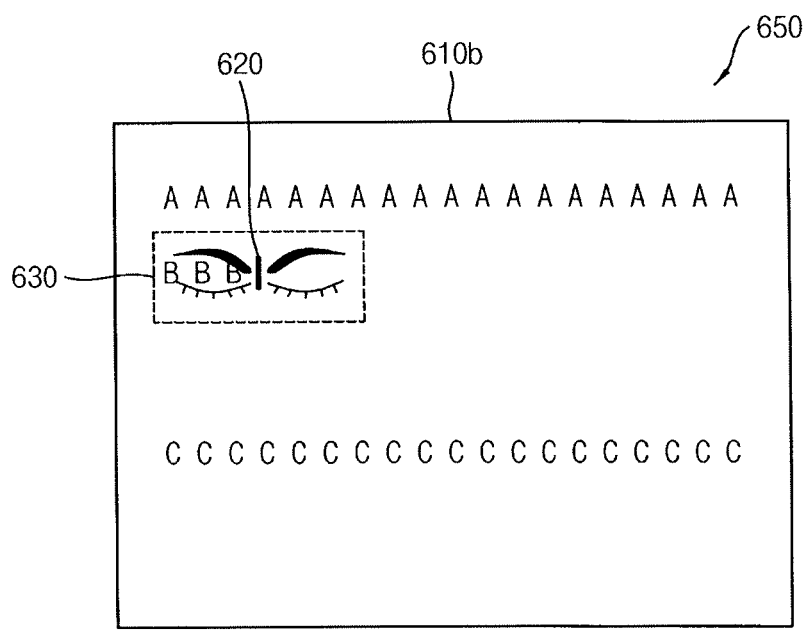
FIG. 8B illustrates an example of a bioeffect image at a user-interested region in FIG. 8A.

FIG. 7 illustrates another embodiment of a method for operating an electronic device to provide a bioeffect image using a display device. FIG. 8A illustrates an example of extracting a user-interested region, and FIG. 8B illustrates an example of a bioeffect image displayed at a user-interested region in FIG. 8A.

Referring to FIG. 7, an electronic device displays a normal image of the original purpose of the electronic device using a display device (S510). The electronic device may detect the position or the coordinate of a cursor of a computer keyboard of the electronic device (S530), and may extract a user-interested region from a region where the normal image is displayed based on the detected cursor position (S550). For example, as illustrated in FIG. 8A, the electronic device may detect the position of the cursor 620 of the computer keyboard at the normal image 610*a*, and may determine, as the user-interested region, a region having the detected position as a center point, a vertex, or the like.

The electronic device may display a bioeffect image at the user-interested region using the display device (S570). In one embodiment, the electronic device may display the bioeffect image instead of the normal image at the user-interested region. In another embodiment, the electronic device may synthesize or overlay the bioeffect image and the normal image at the user-interested region. For example, as illustrated in FIG. 8B, the electronic device may display a synthesized image 650 where a bioeffect image 630 (e.g., an eye-blink inducing image) is synthesized to a normal image 610*b* at the user-interested region determined based on the detected position of the cursor 620.

The aforementioned embodiments may extract the user-interested region based on the cursor position of the computer keyboard, and may display the bioeffect image at the user-interested region, to thereby enhance the effect by the bioeffect image.

Figure 10B:
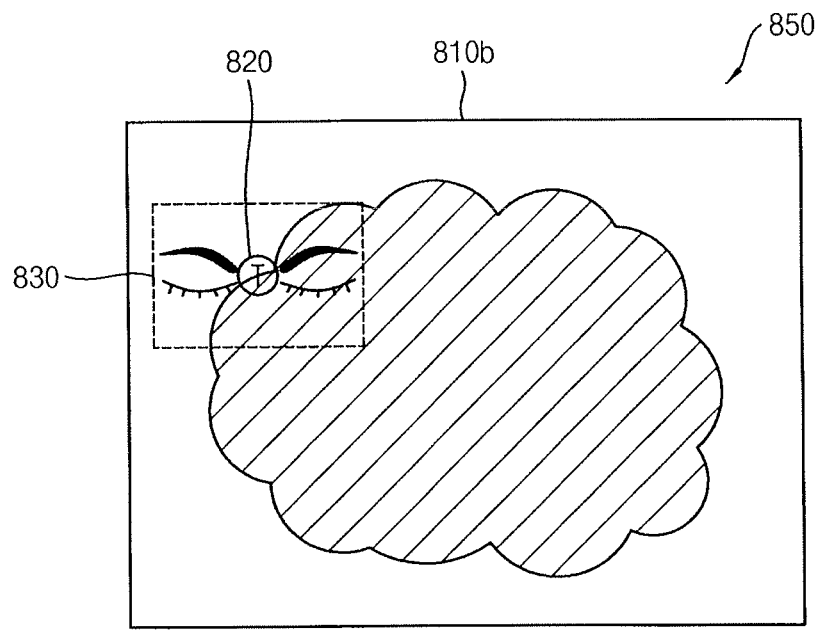
FIG. 10B illustrates an example of a bioeffect image at a user-interested region in FIG. 10A.

FIG. 9 illustrates an embodiment of a method for operating an electronic device to provide a bioeffect image. FIG. 10A illustrates an example of extracting a user-interested region, and FIG. 10B illustrates an example of a bioeffect image displayed at a user-interested region in FIG. 10A.

Referring to FIG. 9, an electronic device displays a normal image of the original purpose of the electronic device using a display device (S710). The electronic device may detect the position or the coordinates of a touch on a touchscreen of the electronic device (S730), and may extract a user-interested region from a region where the normal image is displayed based on the detected touch position (S750). For example, as illustrated in FIG. 10A, the electronic device may detect the position of the touch 820 by a finger 825 of a user at the normal image 810a, and may determine, as the user-interested region, a region having the detected position as a center point, a vertex, or the like.

The electronic device may display a bioeffect image at the user-interested region using the display device (S770). In one embodiment, the electronic device may display the bioeffect image instead of the normal image at the user-interested region. In another embodiment, the electronic device may synthesize or overlay the bioeffect image and the normal image at the user-interested region. For example, as illustrated in FIG. 10B, the electronic device may display a synthesized image 850 where a bioeffect image 830 (e.g., an eye-blink inducing image) is synthesized to a normal image 810b at the user-interested region determined based on the detected position of the touch 820.

The aforementioned method embodiment may extract the user-interested region based on the position of the touch on the touchscreen, and may display the bioeffect image at the user-interested region, to thereby enhance the effect by the bioeffect image.

Figure 11:
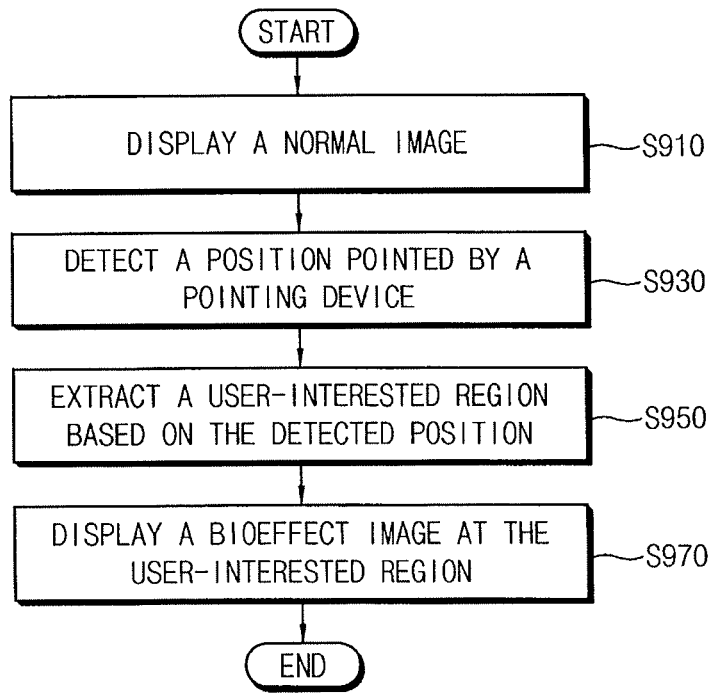
FIG. 11 illustrates another embodiment of method for providing a bioeffect image.
Figure 12A:
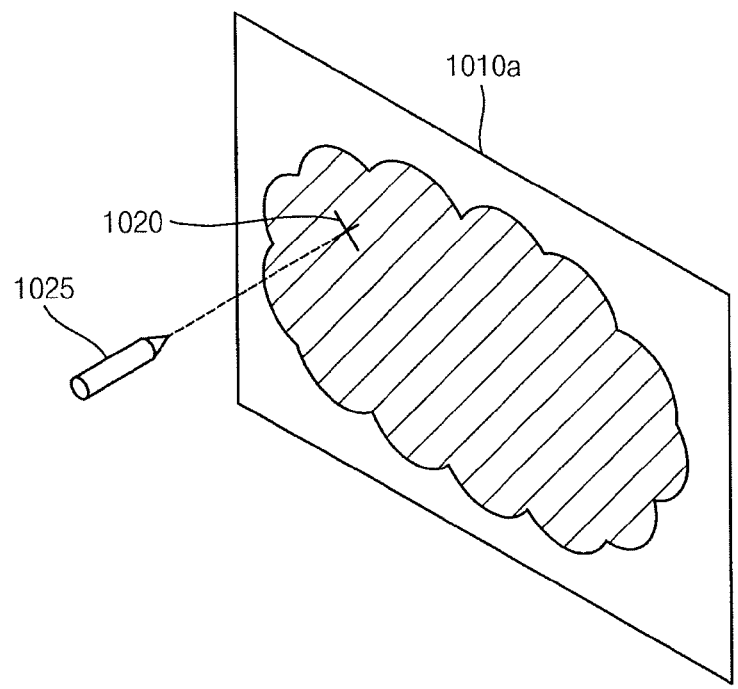
FIG. 12A illustrates another example of extracting a user-interested region.
Figure 12B:
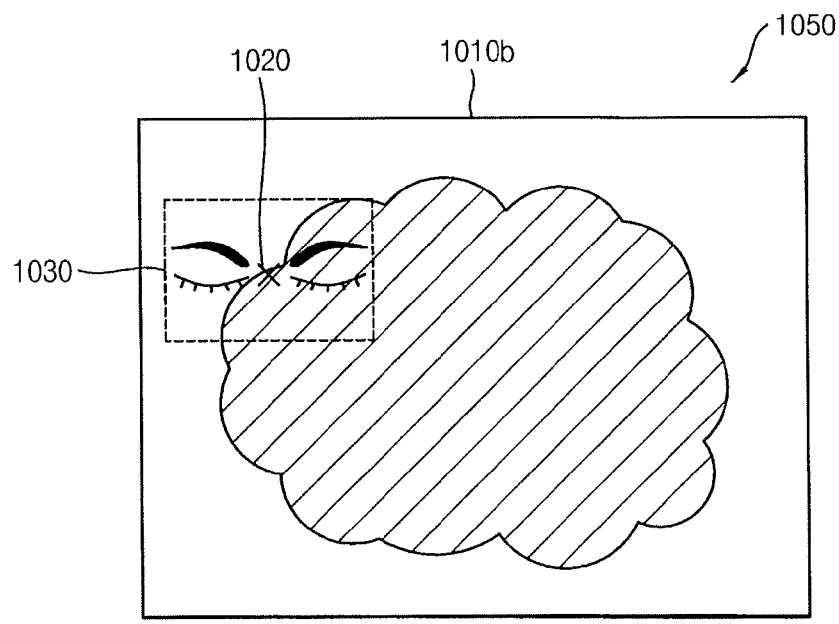
FIG. 12B illustrates an example of a bioeffect image at a user-interested region in FIG. 12A.

FIG. 11 illustrates another embodiment of a method for operating an electronic device to provide a bioeffect image using a display device. FIG. 12A illustrates an example of extracting a user-interested region, and FIG. 12B illustrates an example of a bioeffect image displayed at a user-interested region in FIG. 12A.

Referring to FIG. 11, an electronic device displays a normal image of the original purpose of the electronic device using a display device (S910). The electronic device may detect the position or coordinates pointed by a pointing device of the electronic device (S930), and may extract a user-interested region from a region where the normal image is displayed based on the pointed position (S950). For example, as illustrated in FIG. 12A, the electronic device may detect the position 1020 pointed by the pointing device 1025 (e.g., a light pen, a stylus, or the like) at the normal image 1010a, and may determine, as the user-interested region, a region having the detected position 1020 as a center point, a vertex, or the like.

The electronic device may display a bioeffect image at the user-interested region using the display device (S970). In one embodiment, the electronic device may display the bioeffect image instead of the normal image at the user-interested region. In another embodiment, the electronic device may synthesize or overlay the bioeffect image and the normal image at the user-interested region. For example, as illustrated in FIG. 12B, the electronic device may display a synthesized image 1050 where a bioeffect image 1030 (e.g., an eye-blink inducing image) is synthesized to a normal image 1010b at the user-interested region determined based on the position 1020 pointed by the pointing device 1025.

The aforementioned method embodiments may extract the user-interested region based on the position pointed by the pointing device, and may display the bioeffect image at the user-interested region, to thereby enhance the effect by the bioeffect image.

Figure 13:
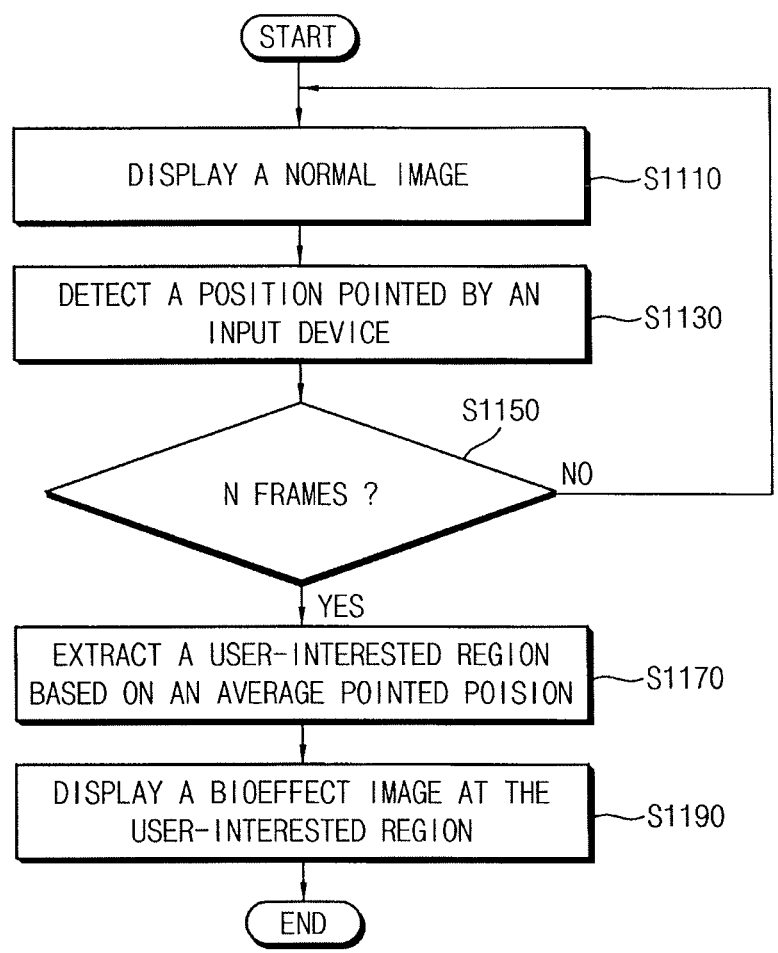
FIG. 13 illustrates another method for providing a bioeffect image.
Figure 14A:
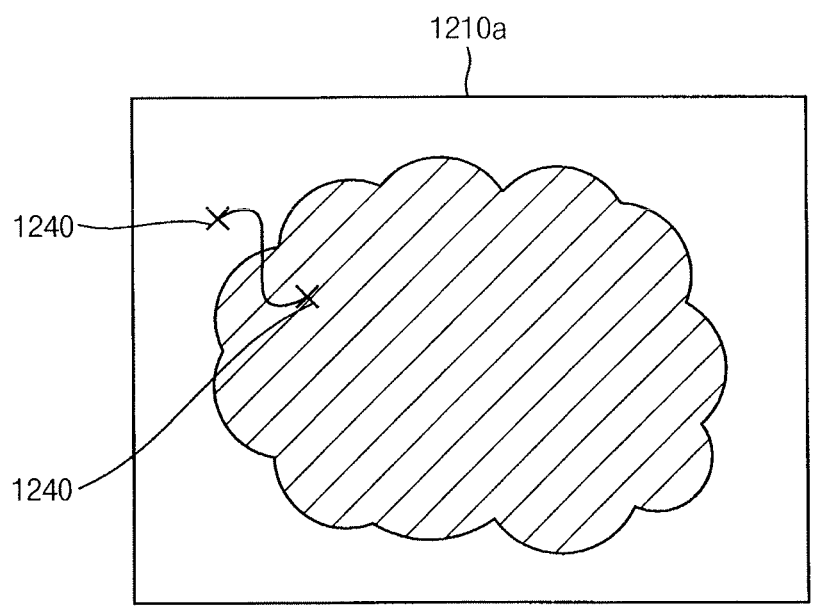
FIG. 14A illustrates another example of extracting a user-interested region.
Figure 14B:
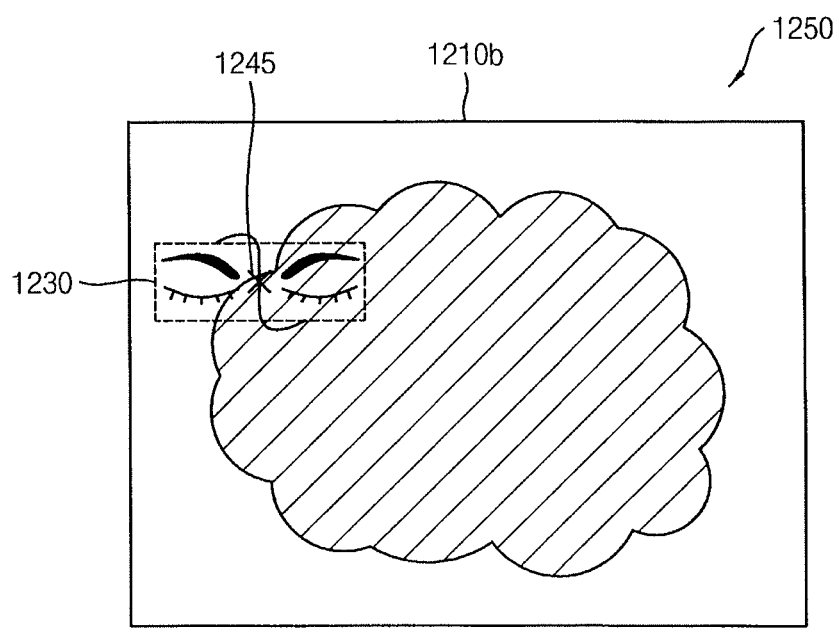
FIG. 14B illustrates an example of a bioeffect image displayed at a user-interested region in FIG. 14A.

FIG. 13 illustrates an embodiment of a method for operating an electronic device to provide a bioeffect image using a display device. FIG. 14A illustrates an example of extraction of a user-interested region, and FIG. 14B illustrates an example of a bioeffect image displayed at a user-interested region in FIG. 14A.

Referring to FIG. 13, an electronic device displays a normal image of the original purpose of the electronic device using a display device (S1110). The electronic device may detect the position or the coordinate pointed by an input device of the electronic device (S1130). In one example, the electronic device may detect a plurality of positions pointed by the input device during a plurality of frames. For example, the electronic device may repeat the pointed position detection until N pointed positions are detected during N frames, where N>1 (S1130 and S1150).

When the N pointed positions are detected during the N frames (S1150: YES), the electronic device may extract a user-interested region from a region where the normal image is displayed based on the N pointed positions. In one example, the electronic device may calculate an average pointed position by averaging the N pointed positions, and may extract the user-interested region based on the average pointed position (S1170).

For example, as illustrated in FIG. 14A, the electronic device may detect a plurality of pointed positions 1240 at the normal image 1210a during a plurality of frames, and may determine, as the user-interested region, a region having the average of the plurality of pointed positions 1240 as a center point, a vertex, or the like.

In another example, the electronic device may calculate a weighted average of the plurality of pointed positions, such that the pointed positions are weighted according to the time of occurrence of the pointed positions. The electronic device may then extract the user-interested region based on the weighted average of the plurality of pointed positions. In another example, the electronic device may calculate a middle position of the plurality of pointed positions, and may extract the user-interested region based on the middle position.

The electronic device may display a bioeffect image at the user-interested region using the display device (S1190). In one example, the electronic device may display the bioeffect image instead of the normal image at the user-interested region. In another example, the electronic device may synthesize or overlay the bioeffect image and the normal image at the user-interested region.

For example, as illustrated in FIG. 14B, the electronic device may display a synthesized image 1250 where a bioeffect image 1230 (e.g., an eye-blink inducing image) is synthesized to a normal image 1210b at the user-interested region determined based on the average pointed position 1245 that is the average of the plurality of pointed positions during the plurality of frames.

The aforementioned embodiments may extract the user-interested region based on the plurality of positions pointed by the input device during the plurality of frames, and may display the bioeffect image at the user-interested region, to thereby enhance the effect by the bioeffect image.

Figure 15:
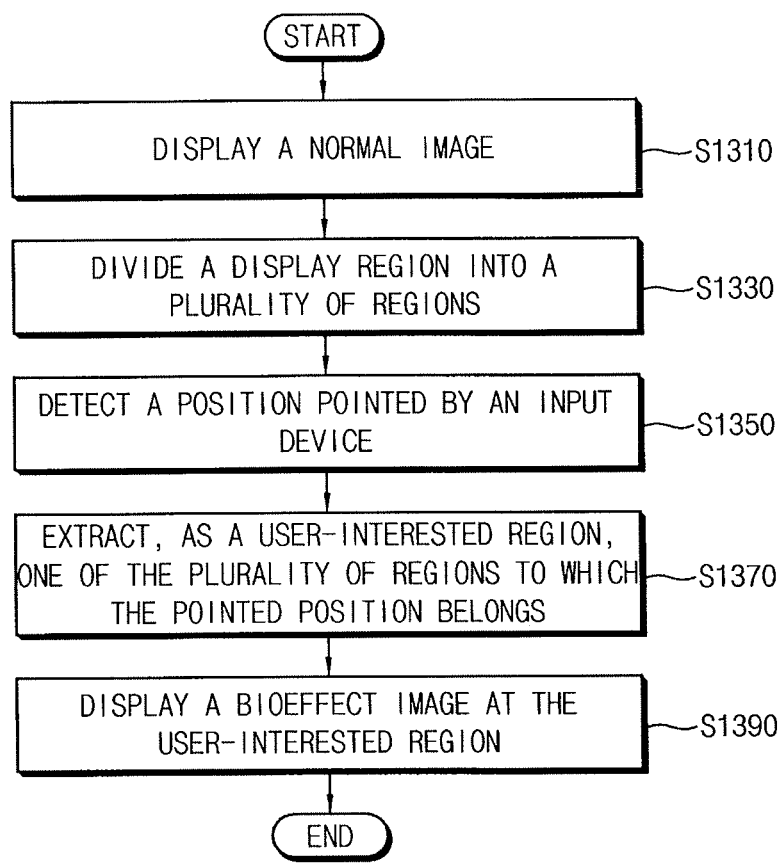
FIG. 15 illustrates another method for providing a bioeffect image.
Figure 16A:
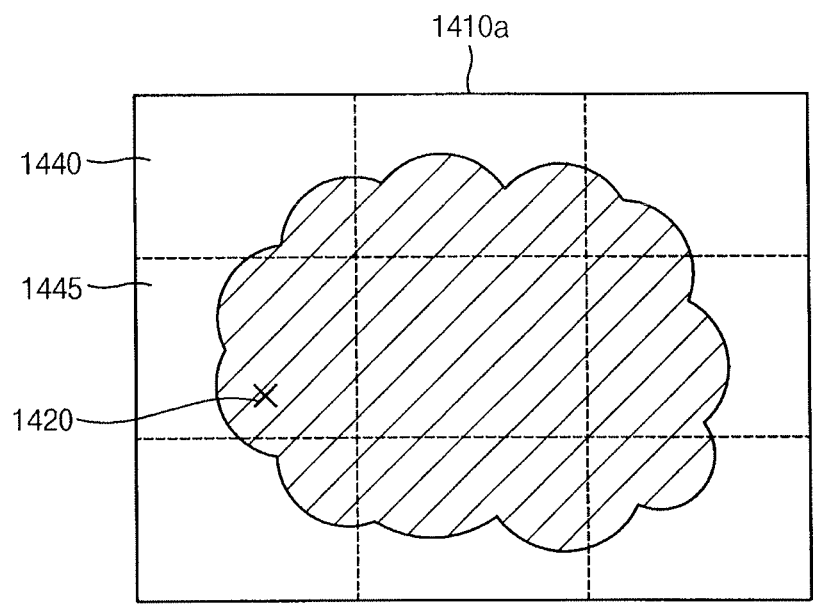
FIG. 16A illustrates an example of extracting a user-interested region.
Figure 16B:
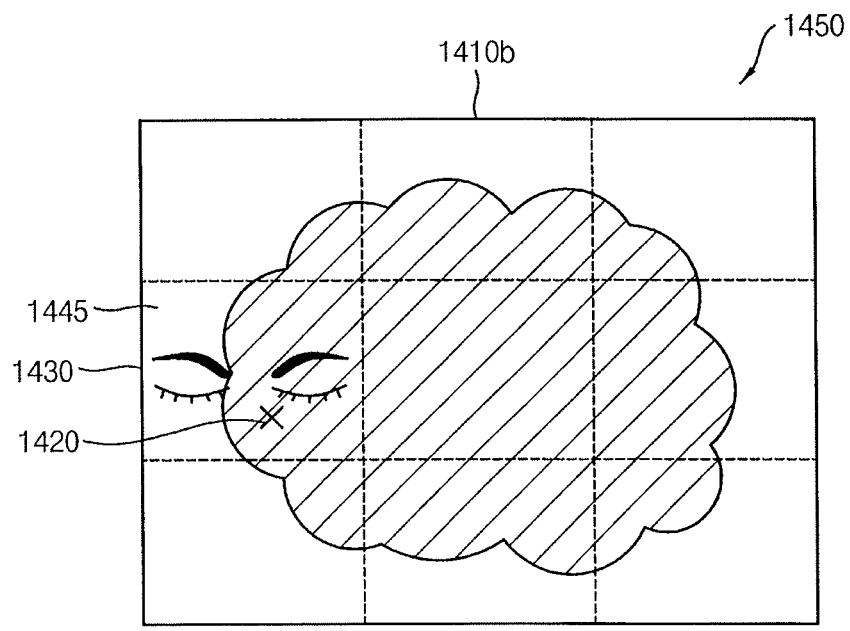
FIG. 16B illustrates an example of a bioeffect image at a user-interested region in FIG. 16A.

FIG. 15 illustrates an embodiment of a method for operating an electronic device to provide a bioeffect image using a display device. FIG. 16A illustrates an example of extracting a user-interested region, and FIG. 16B illustrates an example of a bioeffect image displayed at a user-interested region in FIG. 16A.

Referring to FIG. 15, an electronic device displays a normal image of the original purpose of the electronic device using a display device (S1310). The electronic device may divide a display region of the display device (or a region where the normal image is displayed) into a plurality of regions (S1330), may detect the position or coordinates pointed by an input device of the electronic device (S1350), and may extract, as a user-interested region, one of the plurality of regions to which the pointed position belongs (S1370).

For example, as illustrated in FIG. 16A, the electronic device may divide the region where the normal image 1410*a* is displayed into nine regions 1440 and 1445, and may decide, as the user-interested region, a region 1445 to which the pointed position 1420 belongs among the nine regions 1440 and 1445.

The electronic device may display a bioeffect image at the user-interested region using the display device (S1390). In one example, the electronic device may display the bioeffect image instead of the normal image at the user-interested region. In another example, the electronic device may synthesize or overlay the bioeffect image and the normal image at the user-interested region. For example, as illustrated in FIG. 16B, the electronic device may display a synthesized image 1450 where a bioeffect image 1430 (e.g., an eye-blink inducing image) is synthesized to a normal image 1410*b* at the region 1445 to which the pointed position 1420 belongs.

The aforementioned embodiments may divide the region where the normal image is displayed into the plurality of regions, and may display the bioeffect image at one of the plurality of regions to which the pointed position belongs, to thereby enhance the effect by the bioeffect image.

Figure 18B:
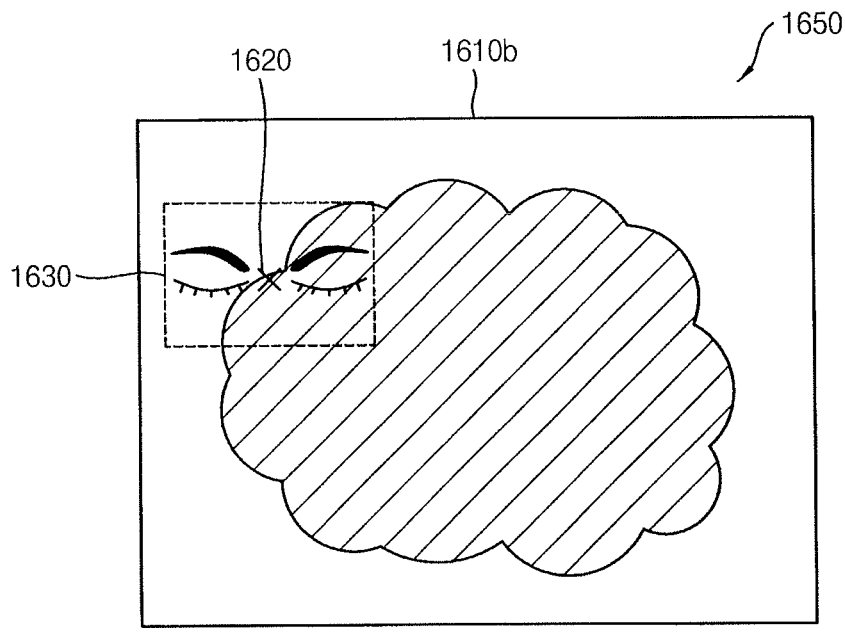
FIG. 18B illustrates an example of a bioeffect image at a user-interested region in FIG. 18A.

FIG. 17 illustrates an embodiment of a method for operating an electronic device to provide a bioeffect image using a display device. FIG. 18A illustrates an example of extraction of a user-interested region, and FIG. 18B illustrates an example of a bioeffect image displayed at a user-interested region in FIG. 18A.

Referring to FIG. 17, an electronic device displays a normal image of the original purpose of the electronic device using a display device (S1510). The electronic device may detect the point of gaze of a user using an image sensor (S1530), and may extract a user-interested region from a region where the normal image is displayed based on the detected point of gaze (S1550). For example, as illustrated in FIG. 18A, the electronic device 1600 may include the image sensor 1660 (e.g., a CMOS image sensor), and may detect the point 1620 of gaze of the user 1625 based on an image captured by the image sensor 1660. The electronic device 1600 may determine, as the user-interested region, a region having the detected point 1620 of gaze of the user 1625 as a center point, a vertex, or the like.

The electronic device may display a bioeffect image at the user-interested region using the display device (S1570). In one example, the electronic device may display the bioeffect image instead of the normal image at the user-interested region. In one example, the electronic device may synthesize or overlay the bioeffect image and the normal image at the user-interested region. For example, as illustrated in FIG. 18B, the electronic device may display a synthesized image 1650 where a bioeffect image 1630 (e.g., an eye-blink inducing image) is synthesized to a normal image 1610*b* at the user-interested region determined based on the detected point 1620 of gaze of the user 1625.

The aforementioned embodiments detect the point of gaze of the user using the image sensor, and display the bioeffect image at the user-interested region determined based on the detected point of gaze, to thereby enhance the effect by the bioeffect image.

Figure 19:
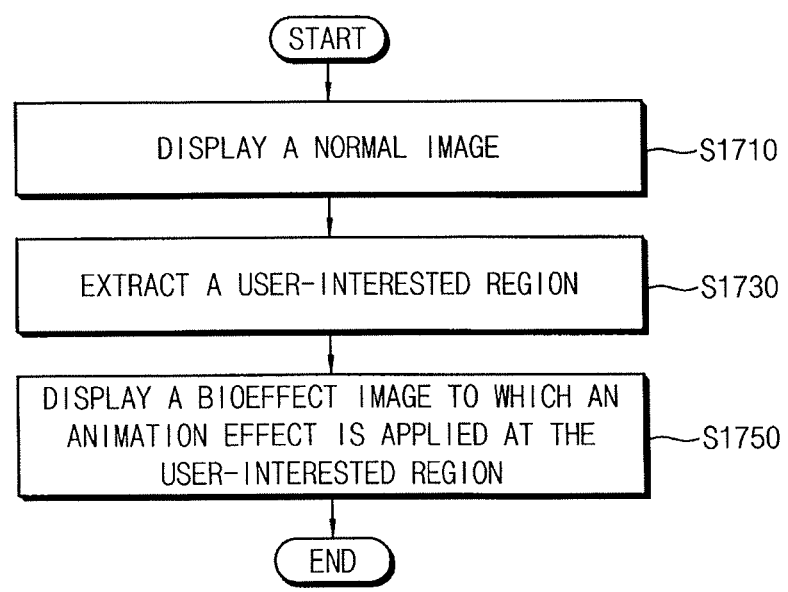
FIG. 19 illustrates another method for providing a bioeffect image.
Figure 20:
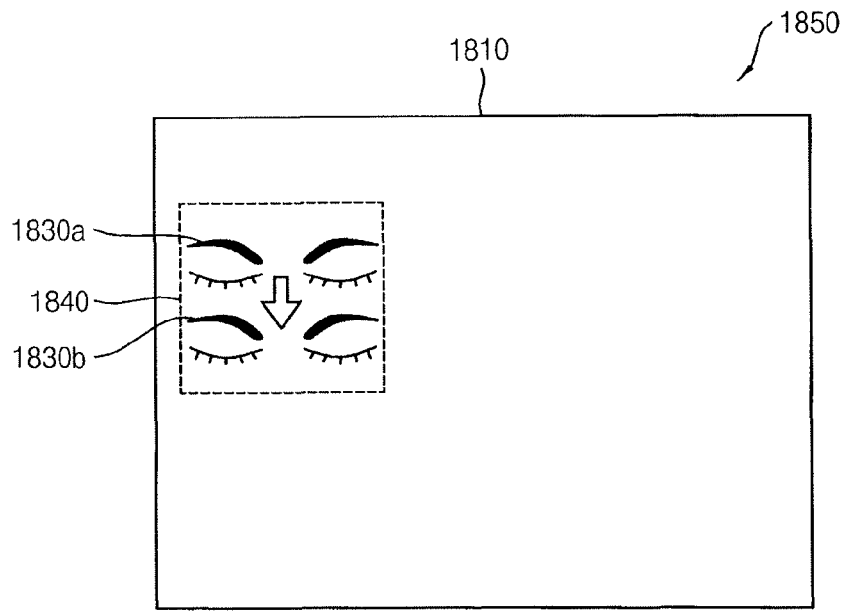
FIG. 20 illustrates an example of a bioeffect image with an animation effect.

FIG. 19 illustrates another embodiment of a method for operating an electronic device to provide a bioeffect image using a display device, and FIG. 20 illustrates an example of a bioeffect image to which an animation effect is applied.

Referring to FIG. 19, an electronic device displays a normal image of the original purpose of the electronic device using a display device (S1710). The electronic device may extract a user-interested region from a display region of the display device, or a region where the normal image is displayed (S1730). In one example, the electronic device may detect a position pointed by an input device of the electronic device, and may extract the user-interested region based on the pointed position. In other example, the electronic device may detect the point of gaze of a user using an image sensor, and may extract the user-interested region based on the detected point of gaze.

The electronic device may display a bioeffect image to which an animation effect is applied at the user-interested region using the display device (S1750). The animation effect may change, for example, any characteristic (e.g., size, position, luminance, color temperature, chrominance, etc.) of the bioeffect image. For example, the animation effect may include at least one of an appear effect, a fly-in effect, a float-in effect, a grow effect a shrink effect, a brightness change effect, a rotation effect, or the like.

For example, as illustrated in FIG. 20, a vertical position change effect is applied to a bioeffect image 1830*a* and 1830*b*, so that an initial bioeffect image 1830*a* is displayed at a first vertical position within a user-interested region and a finial bioeffect image 1830*b* is displayed at a second vertical position within the user-interested region. Also, a synthesized image 1850 may be displayed where the bioeffect image 1830*a* and 1830*b*, to which the vertical position change effect is applied, is synthesized to a normal image 1810*b*. In other embodiments, a different animation effect may be included for any characteristic change of the bioeffect image.

The aforementioned method embodiments display the bioeffect image to which the animation effect is applied, to thereby allow the user to have concentration on the bioeffect image and to enhance the effect by the bioeffect image.

Figure 21:
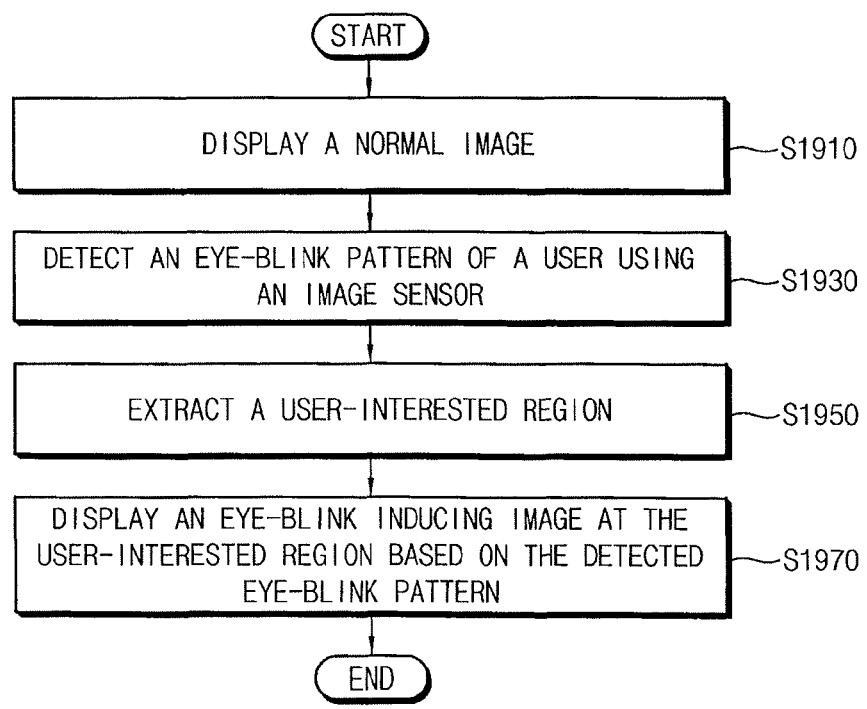
FIG. 21 illustrates an embodiment of a method for providing an eye-blink inducing image.
Figure 22A:
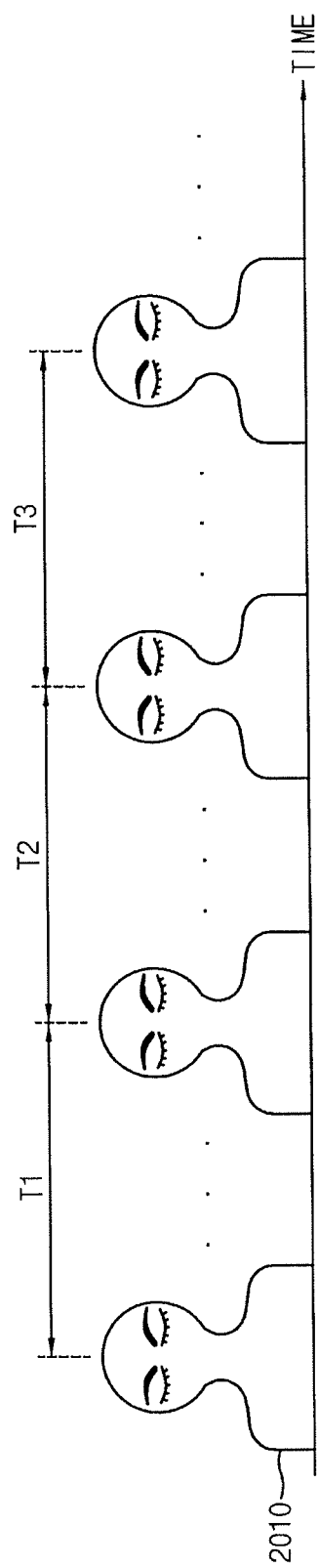
FIG. 22A illustrates an example of an eye-blink pattern of a user detected by an image sensor.

FIG. 21 illustrates an embodiment of a method of operating an electronic device to provide an eye-blink inducing image using a display device. FIG. 22A illustrates an example of an eye-blink pattern of a user detected by an image sensor, and FIG. 22B illustrates an example of an eye-blink inducing image displayed based on the detected eye-blink pattern.

Referring to FIG. 21, an electronic device displays a normal image of the original purpose of the electronic device using a display device (S1910). The electronic device may detect an eye-blink pattern of a user using an image sensor (S1930). Detecting the eye-blink pattern may include a period of the eye-blink (or a time interval between adjacent eye-blinks) and/or duration of the eye-blink (or a time from initiation of the eye-blink to completion of the eye-blink). For example, as illustrated in FIG. 22A, the electronic device may detect a period T1, T2 and T3 (or a time interval) of an eye-blink of a user. The electronic device may extract a user-interested region from a display region of the display device, or a region where the normal image is displayed (S1950).

The electronic device may display an eye-blink inducing image at the user-interested region based on the detected eye-blink pattern (S1970). In one example, the electronic device may display the eye-blink inducing image with the detected period (or the detected time interval) of the eye-blink and/or the detected duration (or the time from initiation to completion) of the eye-blink.

In one example, as illustrated in FIG. 22B, the electronic device may display the eye-blink inducing image 2030 with a period substantially the same as the detected period T1, T2 and T3. Because the eye-blink inducing image is displayed based on the eye-blink pattern of the user, inconvenience to the user may be reduced compared with the case where the eye-blink inducing image is displayed with a fixed period.

The aforementioned method embodiments detect the eye-blink pattern of the user using the image sensor, and display the eye-blink inducing image based on the detected eye-blink pattern, to thereby reduce inconvenience to the user. Further, these embodiments display the eye-blink inducing image at the user-interested region, to thereby enhance the effect by the eye-blink inducing image.

Figure 23:
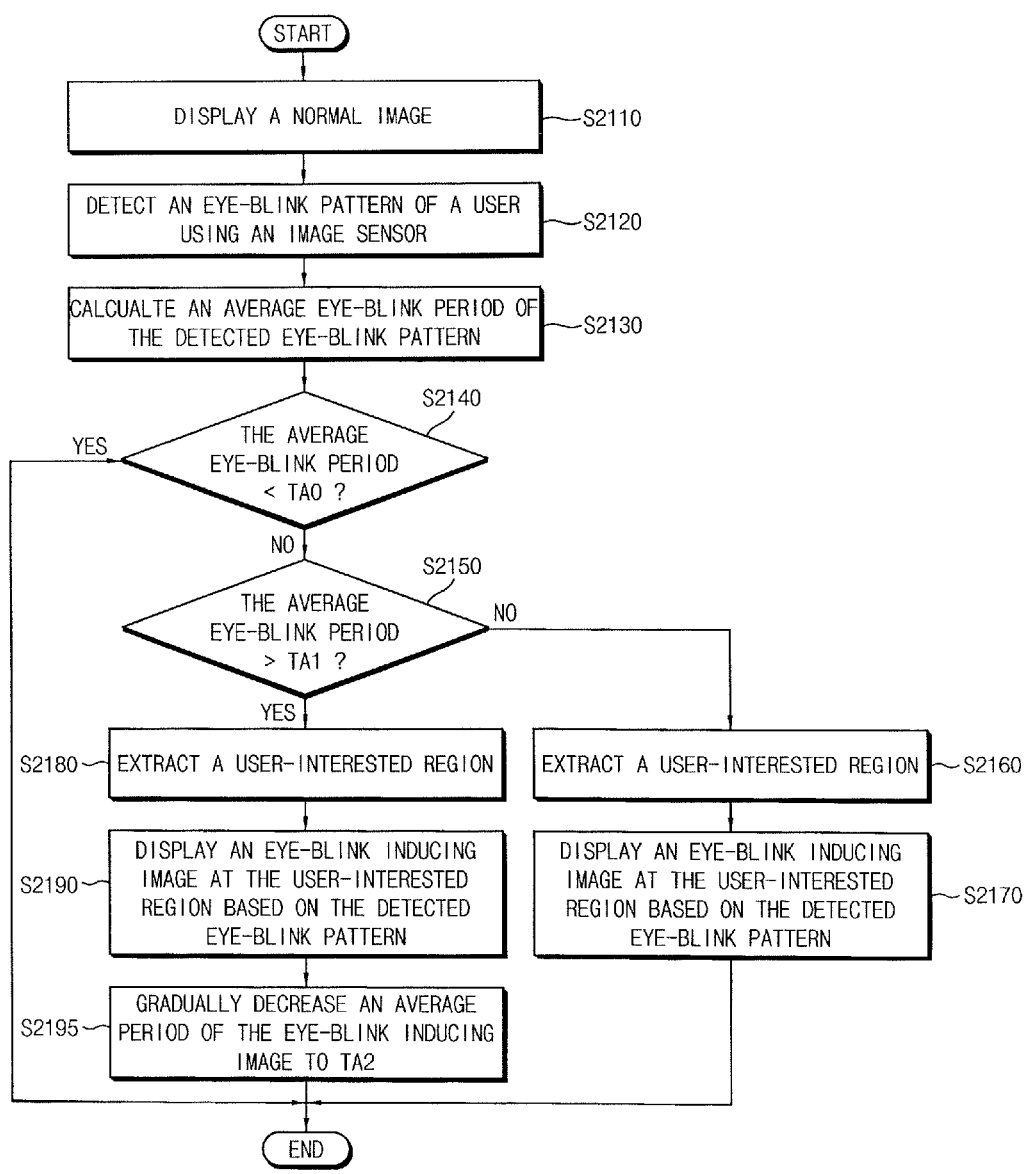
FIG. 23 illustrates another method for providing an eye-blink inducing image.
Figure 24:
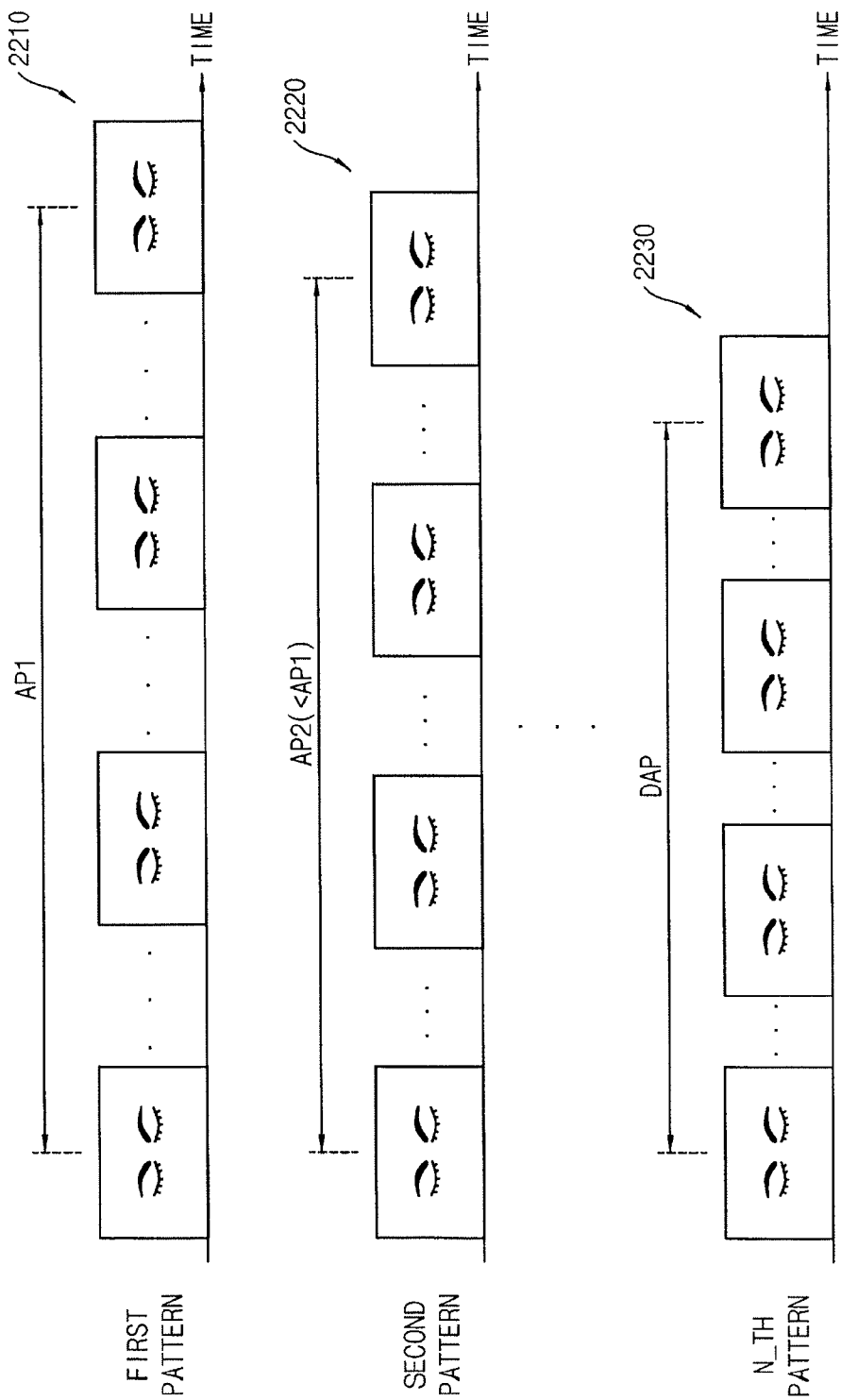
FIG. 24 illustrates an example of an eye-blink inducing image displayed based on a pattern having an average period that gradually decreases.

FIG. 23 illustrates another embodiment of a method for operating an electronic device to provide an eye-blink inducing image using a display device. FIG. 24 illustrates an example of an eye-blink inducing image displayed based on a pattern having an average period that gradually decreases.

Referring to FIG. 23, an electronic device displays a normal image of the original purpose of the electronic device using a display device (S2110). The electronic device may detect an eye-blink pattern of a user using an image sensor (S2120). The electronic device may calculate an average eye-blink period based on the detected eye-blink pattern (S2130). If the average eye-blink period is shorter than a predetermined time TA0 (S2140: YES), the electronic device may not display an eye-blink inducing image. For example, the predetermined time TA0 may be about 4 seconds, and the electronic device may not display the eye-blink inducing image when the user blink eyes with a period shorter than about 4 seconds (or where the user blink eyes more than 15 times per minute).

If the average eye-blink period is longer than or equal to the predetermined time TA0 and shorter than or equal to a first time TA1 (S2140: NO and S2150: NO), the electronic device may extract a user-interested region (S2160), and may display the eye-blink inducing image at the user-interested region based on the detected eye-blink pattern (S2170).

If the average eye-blink period is longer than the first time TA1 (S2140: NO and S2150: YES), the electronic device may extract a user-interested region (S2180), may display the eye-blink inducing image at the user-interested region based on the detected eye-blink pattern (S2190). The electronic device may then gradually decrease a period or average period of the eye-blink inducing image to a second time TA2.

For example, as illustrated in FIG. 24, the electronic device may display the eye-blink inducing image in a first pattern 2210 that is substantially the same as the detected eye-blink pattern. Thereafter, the electronic device may display the eye-blink inducing image in a second pattern 2220 with an average period AP2 that is decreased from an average period AP1 of the eye-blink inducing image in the first pattern 2210.

In a similar manner, the average period of the eye-blink inducing image may be gradually decreased, and, in an Nth pattern 2230, the eye-blink inducing image may be displayed with the average period DAP of the second time TA2, or a desired average period DAP. For example, the desired average period DAP may be about 4 seconds. Because the eye-blink inducing image is first displayed in the detected eye-blink pattern of the user, and the average period of the eye-blink inducing image is gradually decreased, a dry eye syndrome may be prevented without inconvenience to the user.

The aforementioned embodiments detect the eye-blink pattern of the user using the image sensor, and display the eye-blink inducing image based on the detected eye-blink pattern, to thereby reduce the inconvenience of the user. Further, these embodiments may gradually decrease the period of the eye-blink inducing image, and thus inconvenience to the user may be further reduced.

Figure 25:
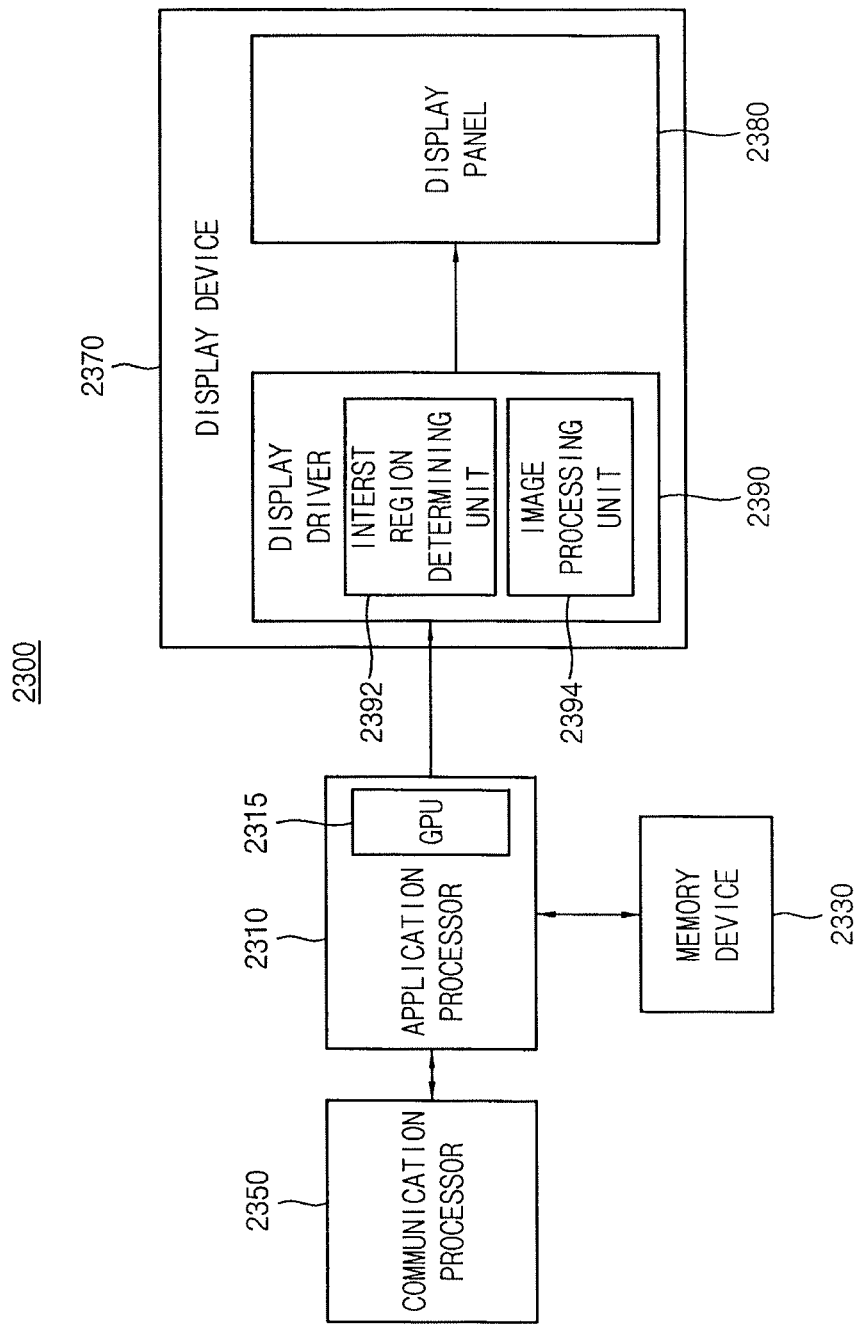
FIG. 25 illustrates an embodiment of an electronic device providing a bioeffect image.

FIG. 25 illustrates an embodiment of an electronic device 2300 providing a bioeffect image. Referring to FIG. 25, the electronic device 2300 includes an application processor 2310, a memory device 2330, a communication processor 2350, and a display device 2370. The electronic device 2300 may be operated in accordance with any of the aforementioned method embodiments.

The application processor 2310 may control an operation of the electronic device 2300. For example, the application processor 2310 may execute an operating system (OS) and various applications (e.g., an internet browser, a game application, a video player, etc.) to control the operation of the electronic device 2300. The application processor 2310 may include a graphic processing unit (GPU) 2315 that controls the display device 2370. The graphic processing unit 2315 may provide the display device 2370 with image data and control signals (e.g., a vertical synchronization signal (VSYNC), a horizontal synchronization signal (HSYNC), a data enable signal (DE), a clock signal (CLK), etc.) for controlling the display device 2370.

The communication processor 2350 performs wired or wireless communication with an external device. For example, the communication processor 2350 may perform an Ethernet communication, near field communication (NFC), radio frequency identification (RFID) communication, mobile telecommunication, memory card communication, universal serial bus (USB) communication, wireless internet, wireless fidelity (Wi-Fi), and/or global positioning system (GPS), Bluetooth (BT).

The communication processor 150 may comprise a baseband chipset and may support global system for mobile communication (GSM), general packet radio system (GPRS), wideband code division multiple access (WCDMA), high speed uplink/downlink packet access (HSxPA), etc. In one embodiment, the application processor 2310 and the communication processor 2350 may be implemented as a single chip. In another embodiment, the application processor 2310 and the communication processor 2350 may be implemented as separate chips.

The memory device 2330 may be coupled to the application processor 2310, and may operate as a main memory. For example, the memory device 2330 may store data processed by the application processor 2310, may store data transferred by the communication processor 2350, and/or may serve as a working memory. For example, the memory device 2330 may be a volatile memory device. Examples include a dynamic random access memory (DRAM), a static random access memory (SRAM), a mobile DRAM, a double data rate (DDR) synchronous DRAM (SDRAM), a low power DDR (LPDDR) SDRAM, or a graphic DDR (GDDR) SDRAM.

Alternatively, the memory device 2330 may be a nonvolatile memory device. Examples include an electrically erasable programmable read-only memory (EEPROM), a flash memory, a phase change random access memory (PRAM), a resistance random access memory (RRAM), a nano floating gate memory (NFGM), a polymer random access memory (PoRAM), a magnetic random access memory (MRAM), or a ferroelectric random access memory (FRAM), etc.

The display device 2370 may be coupled to the application processor 2310, and may display an image based on the image data provided by the graphic processing unit 2315 in the application processor 2310. The display device 2370 may include a display panel 2380 that displays an image, and a display driver 2390 that drives the display panel 2380. In one embodiment, the display panel 2380 may be any type of display panel, such as but not limited to an organic light emitting display (OLED) panel, a liquid crystal display (LCD) panel, or a plasma display panel (PDP).

The display driver 2390 may receive the image data from the graphic processing unit 2315, and may drive the display panel 2380 based on the image data to display a normal image corresponding to the image data. In one embodiment, the display driver 2390 may be implemented as one chip.

The display driver 2390 may include an interest region determining unit 2292 that extracts a user-interested region from a region where the normal image is displayed, and an image processing unit 2394 that inserts a bioeffect image at the user-interested region instead of the normal image, and/or overlays or synthesizes the bioeffect image to the normal image at the user-interested region. For example, the interest region determining unit 2292 may determine the user-interested region based on the position of a touch on a touchscreen of the display device 2370. The image processing unit 2394 may perform an image process to display the bioeffect image at the user-interested region.

The aforementioned embodiments of the electronic device 2300 display the bioeffect image at the user-interested region, to thereby enhance the effect by the bioeffect image.

Figure 26:
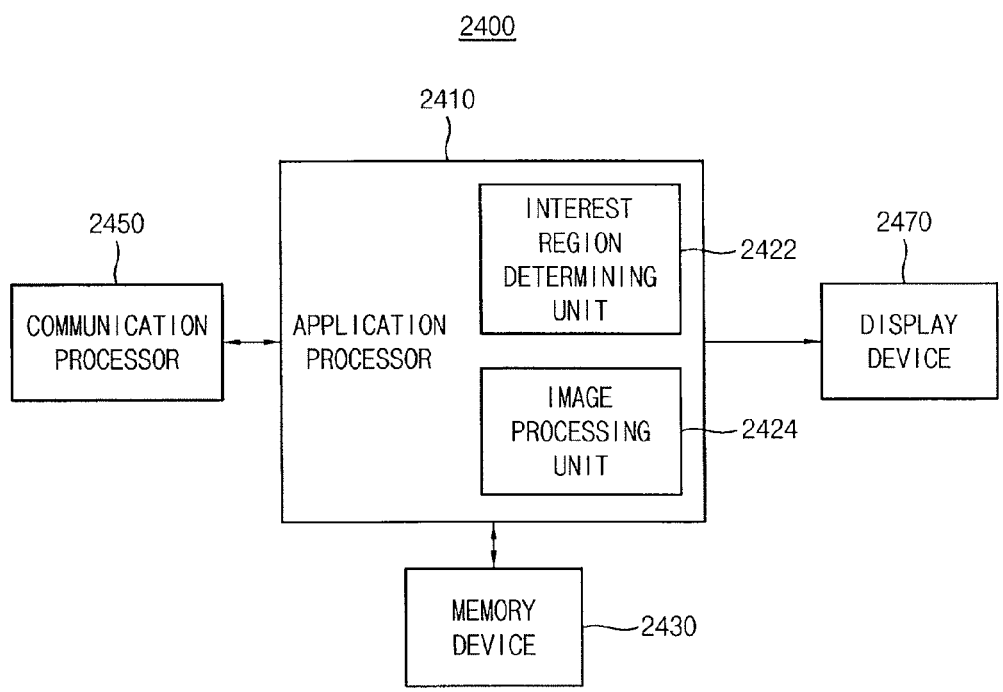
FIG. 26 illustrates another embodiment of an electronic device providing a bioeffect image.

FIG. 26 illustrates another example of an electronic device 2400 providing a bioeffect image. Referring to FIG. 26, the electronic device 2400 includes an application processor 2410, a memory device 2430, a communication processor 2450 and a display device 2470. The electronic device 2400 may be operated in accordance with any of the aforementioned method embodiments. The electronic device 2400 of FIG. 26 may have a similar configuration to an electronic device 2300 of FIG. 25, except that an interest region determining unit 2422 and an image processing unit 2424 are implemented inside the application processor 2410.

The interest region determining unit 2422 may extract a user-interested region. For example, the interest region determining unit 2422 may extract the user-interested region based on a position pointed by an input device of the electronic device 2400. The image processing unit 2424 may insert a bioeffect image at the user-interested region instead of a normal image, or may overlay or synthesize the bioeffect image to the normal image at the user-interested region.

The aforementioned embodiments of the electronic device 2400 display the bioeffect image at the user-interested region, to thereby enhance the effect by the bioeffect image.

Figure 27:
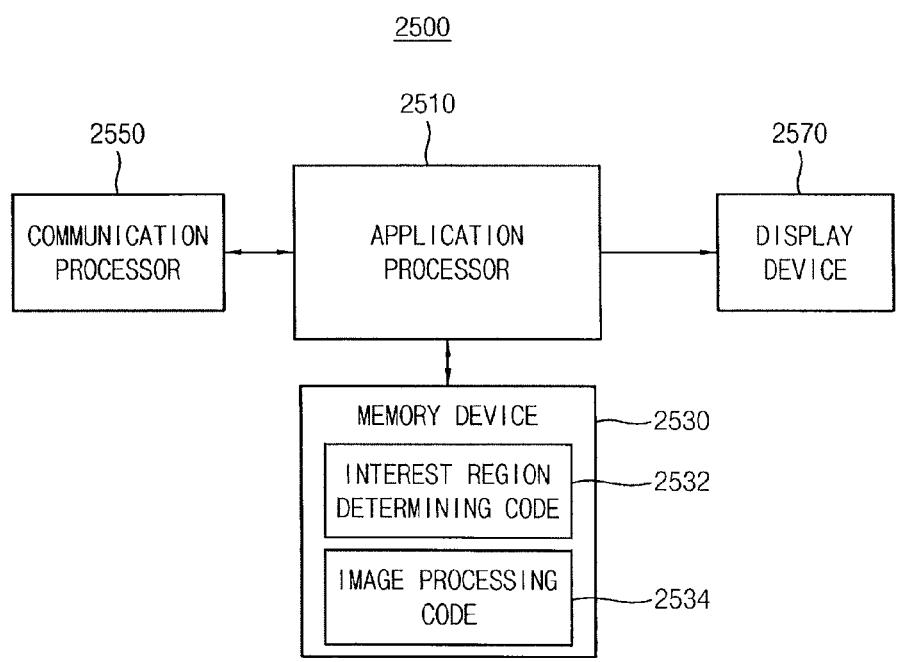
FIG. 27 illustrates another embodiment of an electronic device providing a bioeffect image.

FIG. 27 illustrates another embodiment of an electronic device 2500 providing a bioeffect image. Referring to FIG. 27, the electronic device 2500 includes an application processor 2510, a memory device 2530, a communication processor 2550, and a display device 2570. The electronic device 2500 may be operated by any of the aforementioned method embodiments. The electronic device 2500 of FIG. 27 may have a similar configuration to an electronic device 2300 of FIG. 25, except that the bioeffect image providing function is performed based on an interest region determining code 2532 and an image processing code 2534 stored in the memory device 2530.

The memory device 2530 may store the interest region determining code 2532 for extracting a user-interested region and the image processing code 2534 for inserting a bioeffect image at the user-interested region instead of a normal image, or for overlaying or synthesizing the bioeffect image to the normal image at the user-interested region. For example, the interest region determining code 2532 may be executed by the application processor 2510 to determine the user-interested region based on the position pointed by an input device of the electronic device 2500. The image processing code 2534 may be executed by the application processor 2510 to insert, overlay or synthesize the bioeffect image to the normal image at the user-interested region. According to one embodiment, the interest region determining code 2532 and the image processing code 2534 may be included in an operating system (OS), or may be implement as a separate executable program.

The aforementioned embodiment of the electronic device 2500 displays the bioeffect image at the user-interested region, to thereby enhance the effect by the bioeffect image.

In accordance with other embodiments, the interest region determining unit may be located at the application processor as illustrated in FIG. 26, and the image processing unit may be located at the display device as illustrated in FIG. 25. In another example, the interest region determining unit and the image processing unit may be implemented by a chip separate from the application processor, the display driver, etc.

Figure 28:
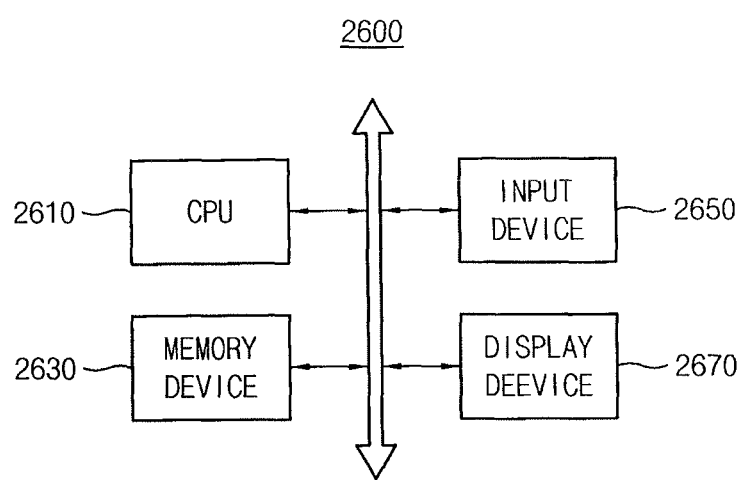
FIG. 28 illustrates another embodiment of an electronic device.

FIG. 28 illustrates an embodiment of an electronic device 2600 which includes a central processing unit (CPU) 2610, a memory device 2630, an input device 2650, and a display device 2670. In one example, the electronic device 2600 may be any type of electronic device. Examples include a personal computer, a server computer, a workstation, a tablet computer, a laptop computer, a cellular phone, a smart phone, a personal digital assistant, a portable multimedia player, a digital camera, a digital television, a set-top box, a music player, a portable game console, a navigation device, etc.

The CPU 2610 may control an operation of the electronic device 2600. For example, the CPU 2610 may perform specific calculations or tasks to control the operation of the electronic device 2600. The CPU 2610 may include a memory controller that controls an operation of the memory device 2630. The memory device 2630 may be coupled to the CPU 2610, and may operate as a main memory of the electronic device 2600. The CPU 2610 may be coupled to an input device 2650 such as but not limited to a mouse, a keyboard, a touchscreen, etc. The CPU 2610 may be further coupled to a display device 2670 such as but not limited to an organic light emitting display (OLED) device, a liquid crystal display (LCD) device, a plasma display panel (PDP) device, etc.

The display device 2670 may display a normal image that the electronic device 2600 displays for an original purpose of the electronic device 2600. A user-interested region may be determined based on the position pointed by the input device 2650 or the point of gaze of a user, and the display device 2670 may display a bioeffect image at the user-interested region. According to one or more embodiments, the bioeffect image may be a behavior inducing image such as but not limited to a biorhythm control image, a color weakness compensation image, or a photo-therapy image.

The aforementioned embodiments of the electronic device 2600 display the bioeffect image at the user-interested region, to thereby enhance the effect by the bioeffect image.

The aforementioned embodiments may be applied to any type of mobile device or computing device. Examples include a cellular phone, a smart phone, a tablet computer, a personal digital assistant, a portable multimedia player, a digital camera, a music player, a portable game console, a navigation system, a video phone, a personal computer, a server computer, a workstation, a tablet computer, and a laptop computer, to name a few.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods described herein.

Also, another embodiment may include a computer-readable medium, e.g., a non-transitory computer-readable medium, for storing the code or instructions described above. The computer-readable medium may be a volatile or nonvolatile memory or other storage device, which may be removably or fixedly coupled to the computer, processor, controller, or other signal processing device which is to execute the code or instructions for performing the method embodiments described herein.

By way of summation and review, bioeffect devices provide only one particular type of treatment. As a result, a user must purchase different bioeffect devices for different treatments. Furthermore, bioeffect devices are not able to display other images (such as visual images) while a user is undergoing treatment.

In accordance with one or more of the aforementioned embodiments, an electronic device extracts a user-interested region from a region where a normal image is displayed, and displays a bioeffect image (e.g., an eye-blink inducing image) at the user-interested region (corresponding to a position pointed by an input device or corresponding to a point of gaze where the user's eyes are located), thereby enhancing the effect by the bioeffect image.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise specifically indicated.

Accordingly, it will be understood by those of skill in the art that various changes in form and details may be made without departing from the spirit and scope of the present invention as set forth in the following claims.

What is claimed is:

1. A method of operating an electronic device, the method comprising:
displaying a first image;
detecting a plurality of positions designated by an input device during a plurality of frames;
calculating an average position by averaging the positions;
identifying a user-interested region from a region including the first image based on the average position; and
displaying a bioeffect image at the user-interested region, wherein the first image and the bioeffect image are different images, and wherein the bioeffect image is a type which is to induce at least one of a therapeutic effect or a predetermined physiological response of a person.

2. The method as claimed in claim 1, wherein:
the input device is a computer mouse, and
each of the positions designated by the input device is a pointer position of the computer mouse.

3. The method as claimed in claim 1, wherein:
the input device is a keyboard, and
each of the positions designated by the input device is a cursor position of the keyboard.

4. The method as claimed in claim 1, wherein:
the input device is a touchscreen, and
each of the positions designated by the input device is a position of a touch on the touchscreen.

5. The method as claimed in claim 1, wherein:
the input device is a pointing device, and
each of the positions designated by the input device is a position pointed by the pointing device.

6. The method as claimed in claim 1, wherein identifying the user-interested region includes:
dividing the region including the first image into a plurality of regions; and
identifying one of the regions corresponding to the average position as the user-interested region.

7. The method as claimed in claim 1, further comprising:
applying an animation effect to the bioeffect image.

8. The method as claimed in claim 7, wherein the animation effect includes at least one of an appear effect, a fly-in effect, a float-in effect, a grow effect, a shrink effect, a brightness change effect, or a rotation effect.

9. The method as claimed in claim 1, wherein the bioeffect image is displayed for a duration shorter than a duration perceptible by a user.

10. The method as claimed in claim 1, wherein the bioeffect image is periodically displayed.

11. The method as claimed in claim 1, wherein at least one of a period of the bioeffect image or a duration of the bioeffect image varies.

12. The method as claimed in claim 1, wherein the bioeffect image includes at least one of a behavior inducing image, a photo-therapy image, a biorhythm control image, or a color weakness compensation image.

13. The method as claimed in claim 1, wherein the bioeffect image is an eye-blink inducing image to induce eye blinking of a user.

14. The method as claimed in claim 13, further comprising:
detecting an eye-blink pattern; and displaying the eye-blink inducing image based on the eye-blink pattern.

15. The method as claimed in claim 13, further comprising:
calculating an average eye-blink period based on a detected eye-blink pattern; and
displaying the eye-blink inducing image if the average eye-blink period is longer than a predetermined time.

16. A method of operating an electronic device, the method comprising:
displaying a first image;
detecting a point of gaze of a user;
identifying a user-interested region from a region including the first image based on the point of gaze; and
displaying a bioeffect image at the user-interested region, wherein the first image and the bioeffect image are different images, and wherein the bioeffect image is a type which is to induce at least one of a therapeutic effect or a predetermined physiological response of a person.

17. A method of operating an electronic device, the method comprising:
displaying a first image;
identifying a user-interested region from a region including the first image;
calculating an average eye-blink period based on a detected eye-blink pattern; and
displaying an eye-blink inducing image that induces eye blinking of a user at the user-interested region if the average eye-blink period is longer than a first time, the eye-blink inducing image displayed based on a pattern having an average period that decreases at a predetermined rate from the first time to a second time shorter than the first time.

* * * * *